United States Patent
Raleigh et al.

(10) Patent No.: US 11,028,137 B2
(45) Date of Patent: Jun. 8, 2021

(54) MUTANT ISLET AMYLOID POLYPEPTIDES WITH IMPROVED SOLUBILITY AND METHODS FOR USING THE SAME

(71) Applicant: The Research Foundation for The State University of New York, Albany, NY (US)

(72) Inventors: Daniel Raleigh, Stony Brook, NY (US); Rehana Akter, Stony Brook, NY (US); Andisheh Abedini, New York, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 16/482,471

(22) PCT Filed: Feb. 1, 2018

(86) PCT No.: PCT/US2018/016348
§ 371 (c)(1),
(2) Date: Jul. 31, 2019

(87) PCT Pub. No.: WO2018/144671
PCT Pub. Date: Aug. 9, 2018

(65) Prior Publication Data
US 2019/0352356 A1    Nov. 21, 2019

Related U.S. Application Data

(60) Provisional application No. 62/453,068, filed on Feb. 1, 2017.

(51) Int. Cl.
*A61K 38/28*   (2006.01)
*A61P 1/00*    (2006.01)
*C07K 14/47*   (2006.01)

(52) U.S. Cl.
CPC .......... *C07K 14/4711* (2013.01); *A61K 38/28* (2013.01)

(58) Field of Classification Search
CPC ....... A61K 38/28; A61K 2300/00; A61P 1/00; C07K 14/4711; C07K 14/47
USPC .......... 514/6.3, 1.1, 7.2, 11.7, 21.3; 530/300, 530/308, 324
See application file for complete search history.

(56) References Cited

U.S. PATENT DOCUMENTS

| | | | |
|---|---|---|---|
| 5,663,294 A | 9/1997 | Colman et al. | |
| 6,610,824 B2 | 8/2003 | Gaeta et al. | |
| 7,550,558 B2 | 6/2009 | Leite et al. | |
| 8,637,575 B2 | 1/2014 | Reuveni et al. | |
| 10,000,543 B2 * | 6/2018 | Schellenberger | ....... A61P 19/02 |
| 10,072,060 B2 | 9/2018 | Raleigh et al. | |
| 2008/0248999 A1 | 10/2008 | Steiner | |
| 2010/0221240 A1 | 9/2010 | Kapurniotu et al. | |
| 2010/0239554 A1 | 9/2010 | Schellenberger et al. | |
| 2014/0087995 A1 | 3/2014 | Dahl et al. | |
| 2014/0221287 A1 | 8/2014 | Sun et al. | |
| 2017/0037088 A1 | 2/2017 | Schellenberger et al. | |
| 2017/0051032 A1 | 2/2017 | Raleigh et al. | |
| 2017/0158748 A1 * | 6/2017 | Schellenberger | ....... A61P 35/00 |
| 2018/0319860 A1 | 11/2018 | Raleigh et al. | |

FOREIGN PATENT DOCUMENTS

| | | |
|---|---|---|
| WO | 93/10146 A1 | 5/1993 |
| WO | 99/34822 A1 | 7/1999 |
| WO | 2013/151729 A1 | 10/2013 |
| WO | WO 2015/168488 A2 | 11/2015 |

OTHER PUBLICATIONS

Abedini A. et al., "Mechanisms of Islet Amyloidosis Toxicity in Type 2 Diabetes", FEBS Letters 587:1119-1127 (2013).
Abedini A. et al., "Recovery and Purification of Highly Aggregation-Prone Disulfide-Containing Peptides: Application to Islet Amyloid Polypeptide", Analytical Biochemistry 351:181-186 (2006).
Abedini A. et al., "Destabilization of Human IAPP Amyloid Fibrils by Proline Mutations Outside of the Putative Amyloidogenic Domain: Is There a Critical Amyloidogenic Domain in Human IAPP?", J. Mol. Biol. 355:274-281 (2006).
Abedini A. et al., "Incorporation of Pseudoproline Derivatives Allows the Facile Synthesis of Human IAPP, a Highly Amyloidogenic and Aggregation-Prone Polypeptide", Organic Letters 7(4):693-696 (2005).
Akter R. et al., "Islet Amyloid Polypeptide: Structure, Function, and Pathophysiology", Journal of Diabetes Research 2016:ID2798269, 18 pages (2016).
Bailey R.J. et al., "Pharmacology of the Human CGRP1 Receptor in Cos 7 Cells", Peptides 27:1367-1375 (2006).
Brender J.R. et al., "A Single Mutation in the Non-Amyloidogenic Region of IAPP (Amylin) Greatly Reduces Toxicity", Biochemistry 47(48):12680-12688 (Dec. 2, 2008).
Camargo D.C.R. et al., "Cloning, Expression and Purification of the Human Islet Amyloid Polylpeptide (hIAPP) from *Escherichia coli*", Protein Expression and Purification 106:49-56 (2015).
Cao P. et al., "Islet Amyloid Polypeptide Toxicity and Membrane Interactions", PNAS 110(48):19279-19284 (Nov. 26, 2013).

(Continued)

*Primary Examiner* — Julie Ha
(74) *Attorney, Agent, or Firm* — Scully, Scott, Murphy & Presser, P.C.

(57) ABSTRACT

Isolated non-naturally occurring, mutant-human islet amyloid polypeptides (IAPP) polypeptides, which are more soluble at neutral pH than the wild-type human islet amyloid polypeptide (hIAPP) protein are disclosed. These polypeptides can be formulated or co-formulated at physiological pH, which enable the polypeptides to be delivered to a subject in a single injection with an insulin agent. Methods and pharmacological compositions for treating an abnormal condition, such as an amyloid-based disease or type-1 diabetes in a subject are also disclosed.

Figure 1:
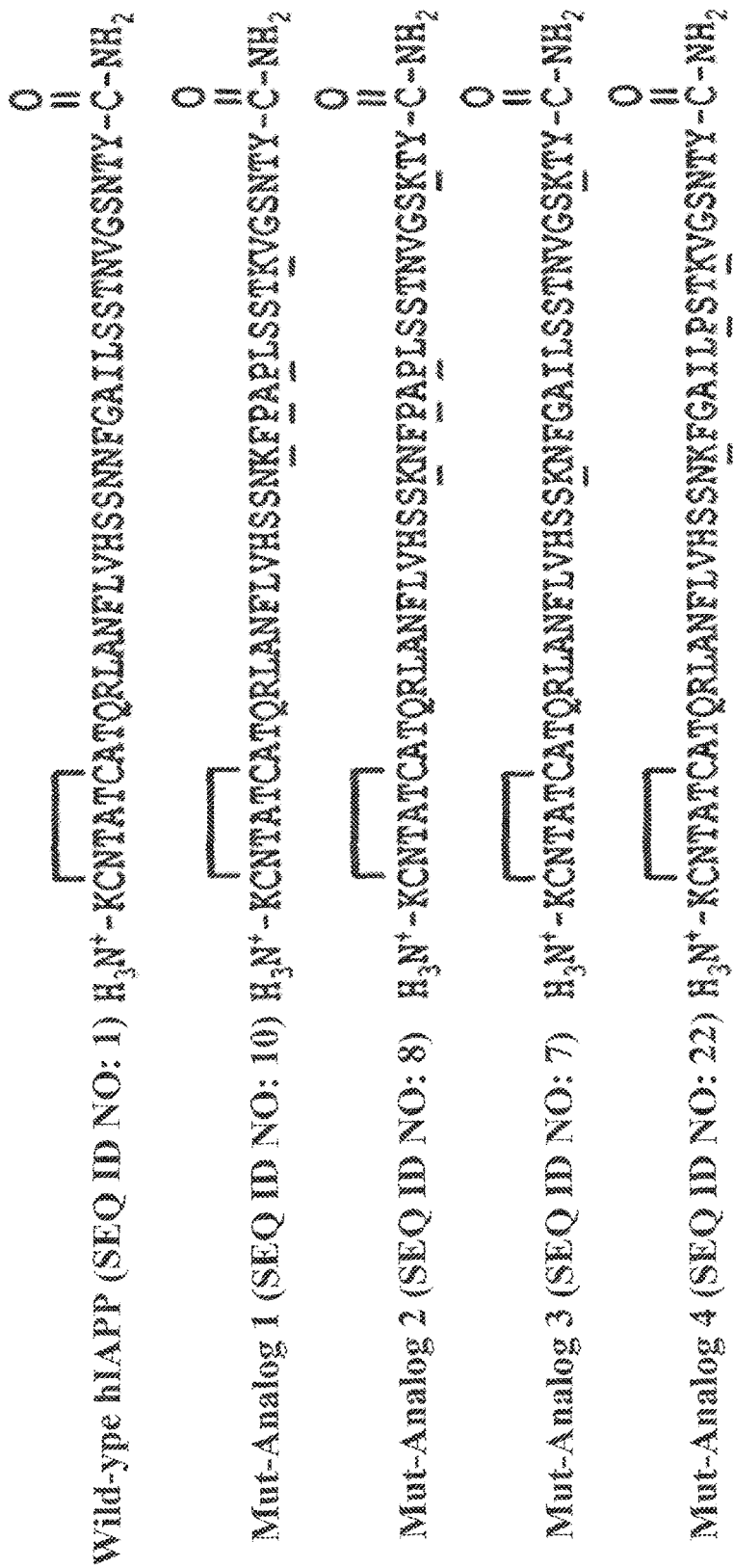
Figure 2A:
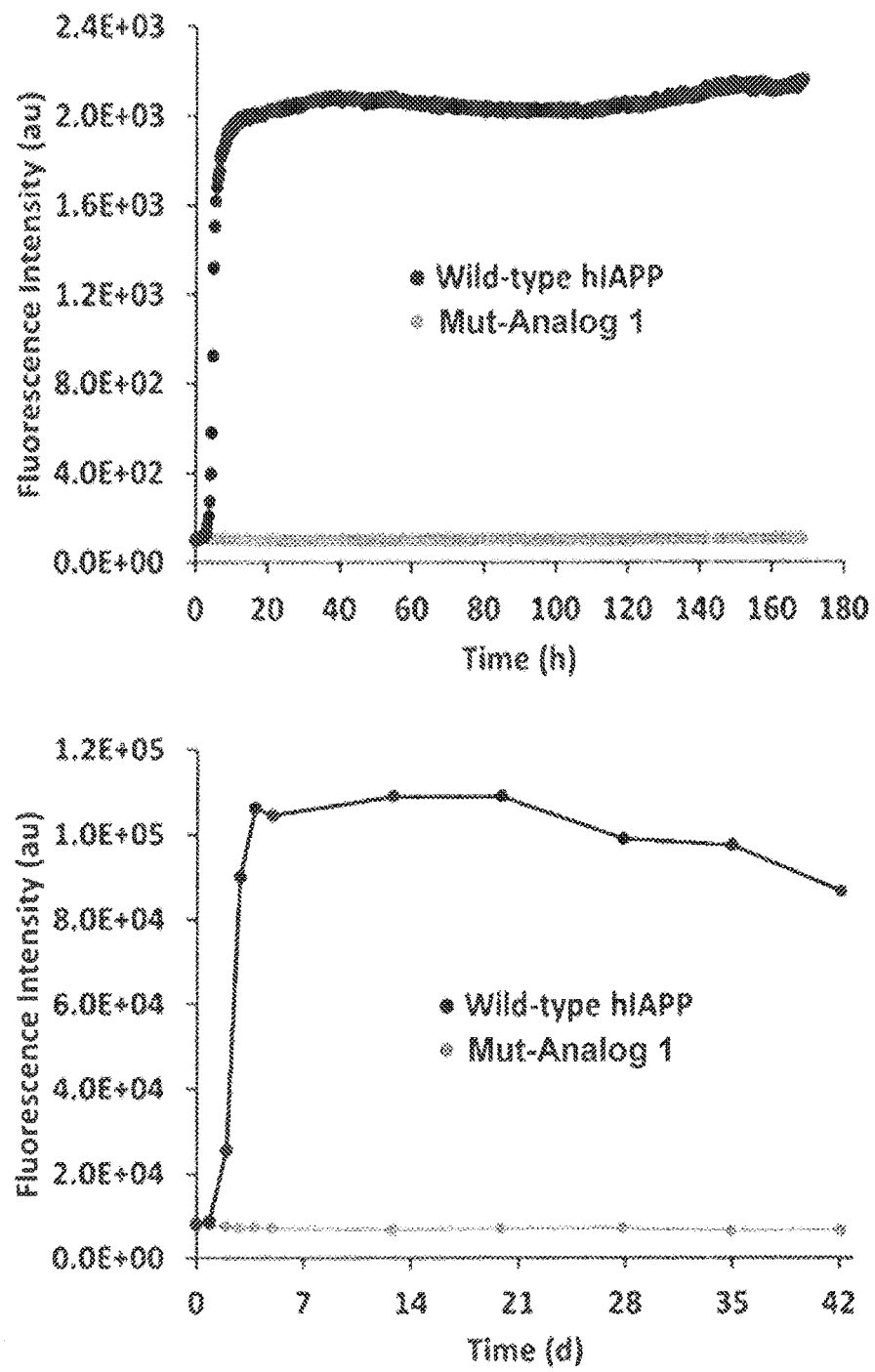
Figure 2B:
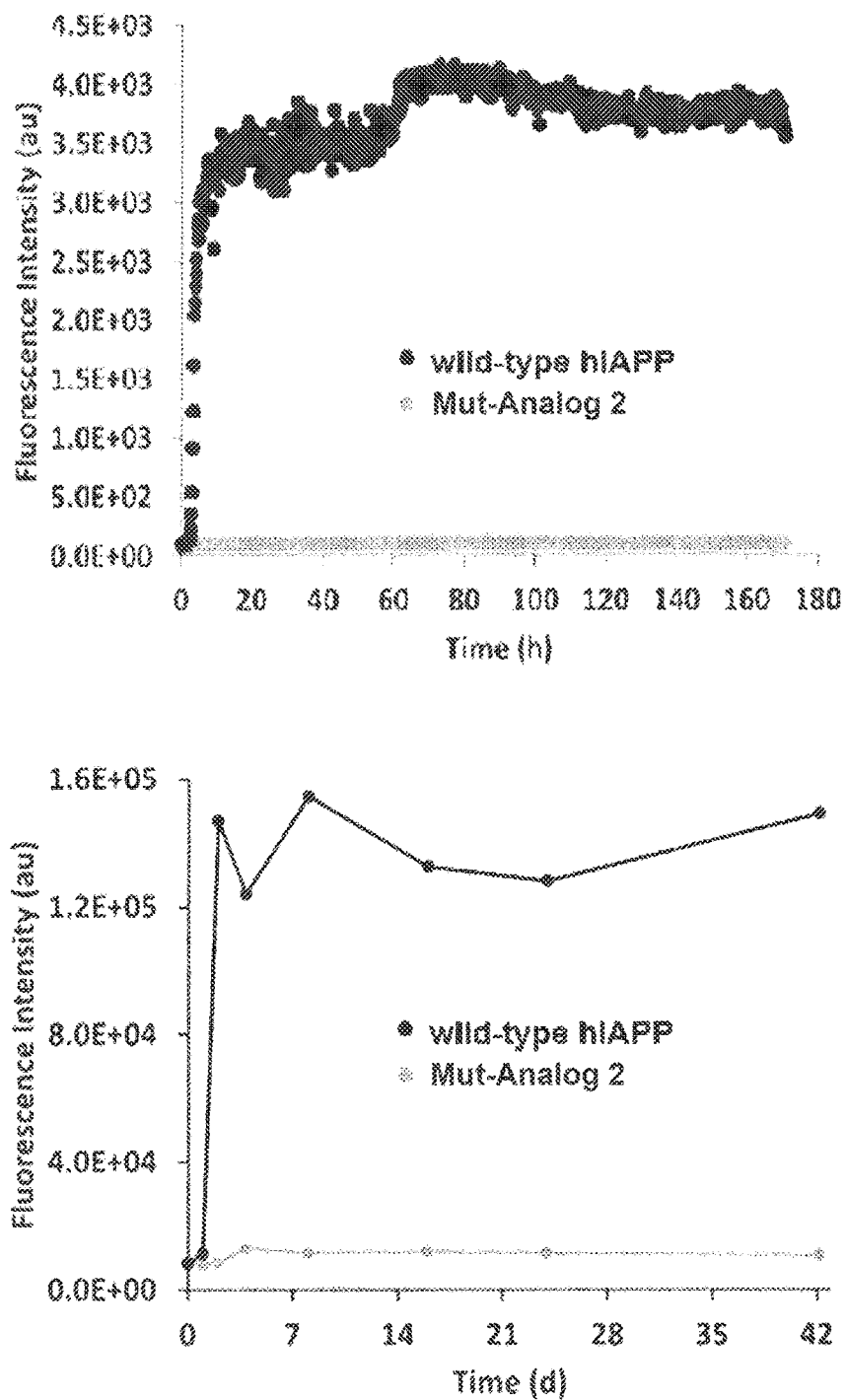
Figure 2C:
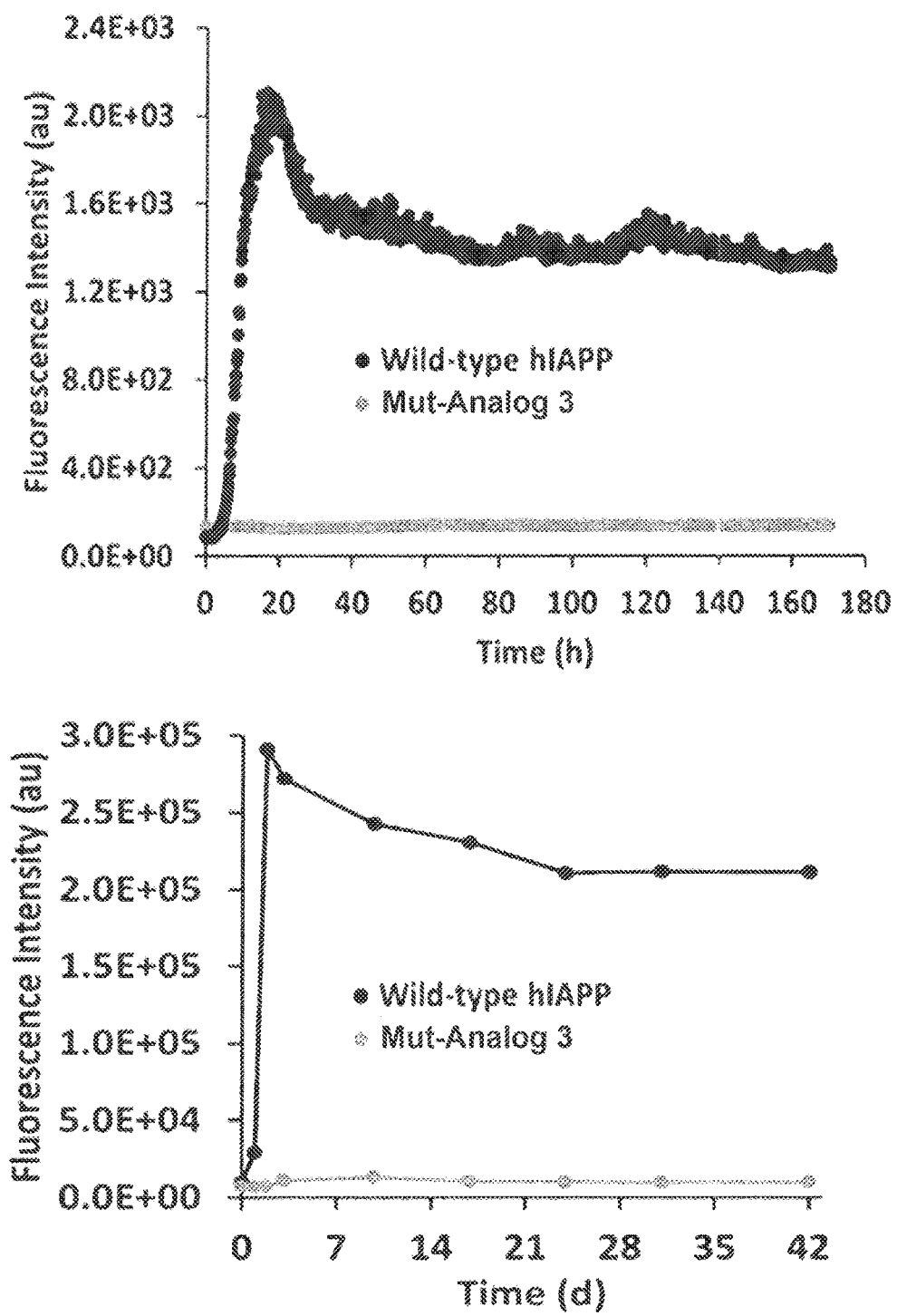
Figure 2D:
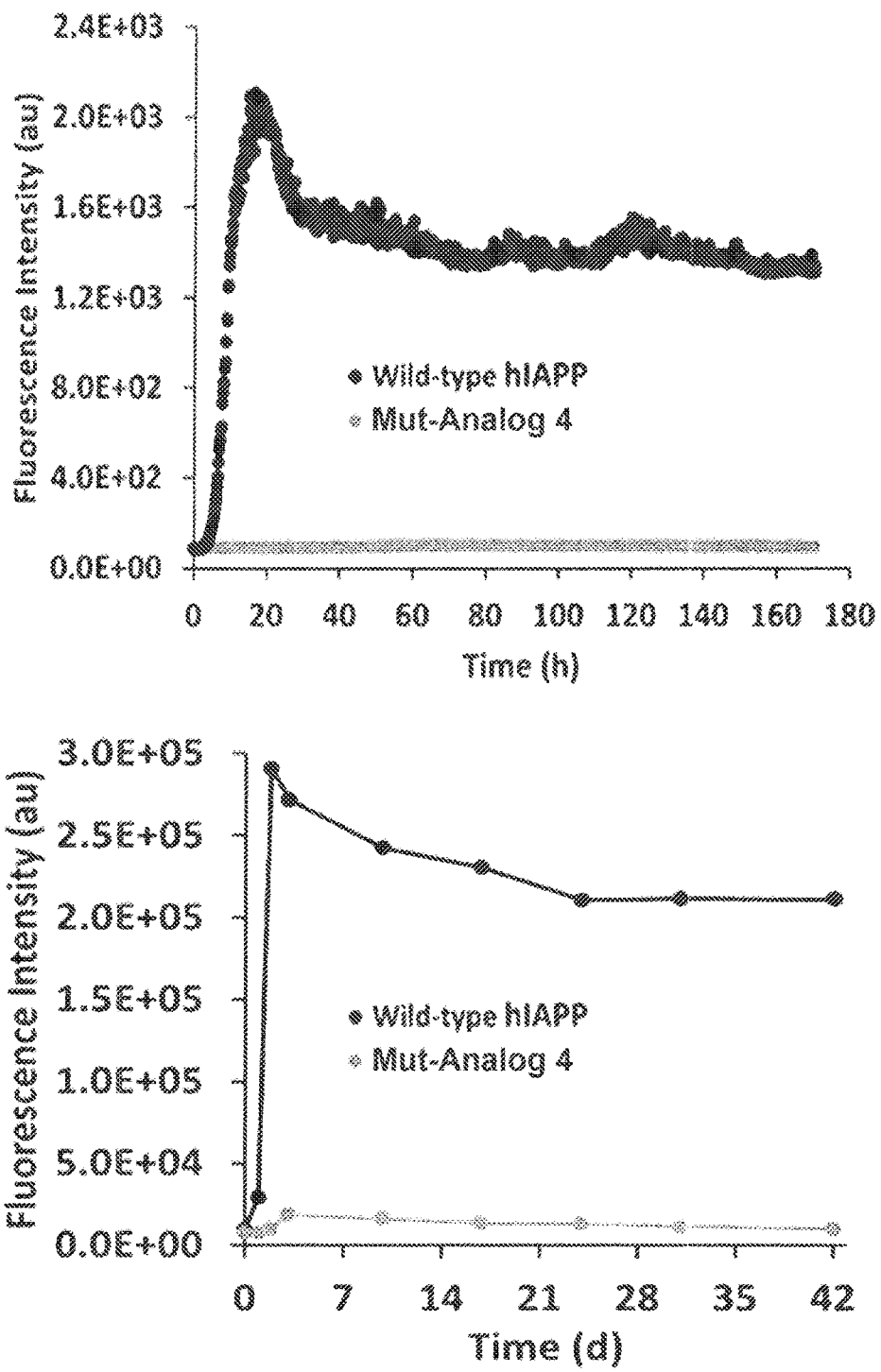
Figure 3A:
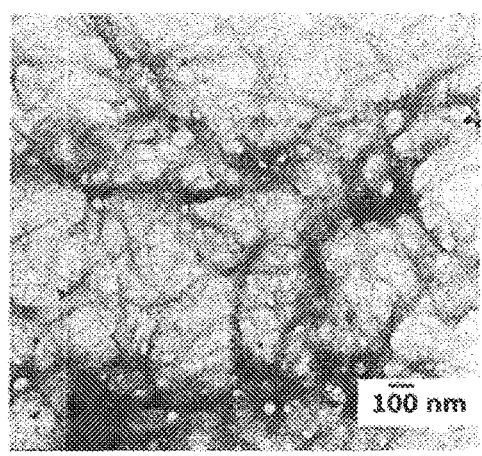
Figure 3B:
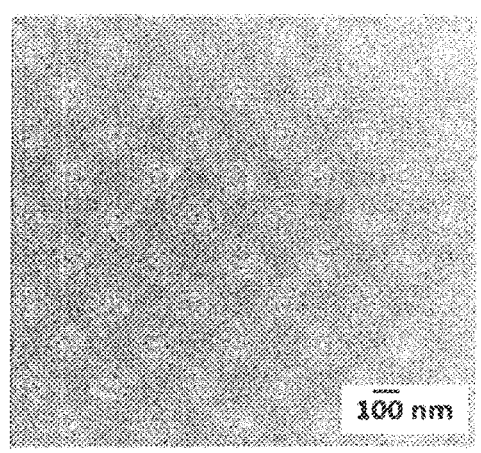
Figure 3C:
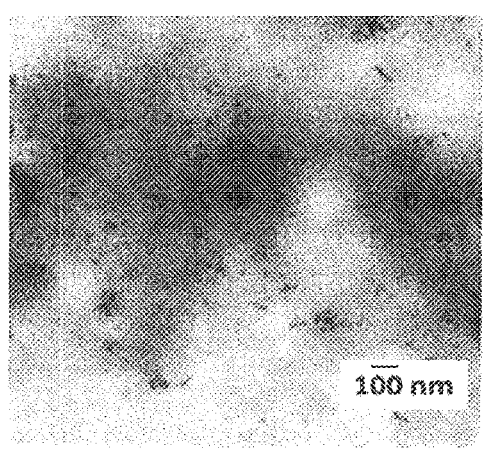
Figure 3D:
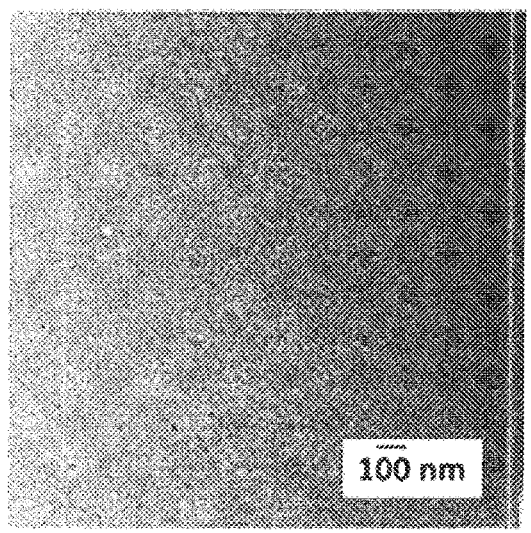
Figure 3E:
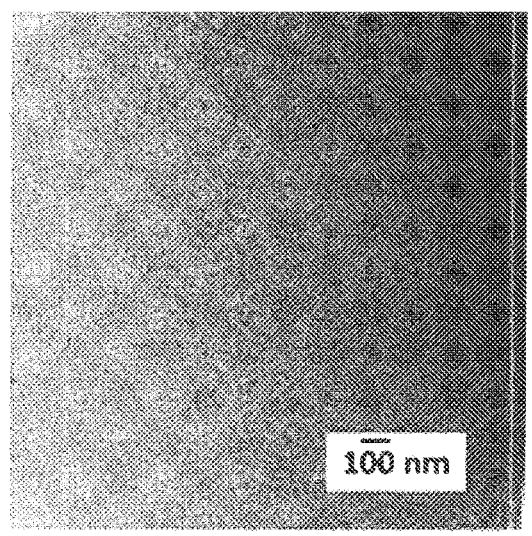

19 Claims, 12 Drawing Sheets
Specification includes a Sequence Listing.

(56) References Cited

OTHER PUBLICATIONS

Cao P. et al., "Islet Amyloid: From Fundamental Biophysics to Mechanisms of Cytotoxicity", FEBS Letters 587:1106-1118 (2013).
Chiu C-C et al., "Effect of Proline Mutations on the Monomer Conformations of Amylin", Biophysical Journal 105:1227-1235 (Sep. 2013).
Clark A. et al., "Islet Amyloid Formed from Diabetes-Associated Peptide May Be Pathogenic in Type-2 Diabetes", The Lancet 330(8553):231-234 (Aug. 1, 1987).
Cooper G.J.S. et al., "Purification and Characterization of a Peptide from Amyloid-Rich Pancreases of Type 2 Diabetic Patients", Proc. Natl. Acad. Sci. USA 84:8628-8632 (Dec. 1987).
During M.J. et al., "Controlled Release of Dopamine from a Polymeric Brain Implant: In Vivo Characterization", Annals of Neurology 25(4):351-356 (1989).
Fox A. et al., "Selection for Nonamyloidogenic Mutants of Islet Amyloid Polypeptide (IAPP) Identifies an Extended Region for Amyloidogenicity", Biochemistry 49:7783-7789 (2010).
Gingell J.J. et al., "A Key Role of Tryptophan 84 in Receptor Activity-Modifying Protein 1 in the Amylin 1 Receptor", Peptides 31:1400-1404 (2010).
Hay D.L. et al., "Pharmacological Discrimination of Calcitonin Receptor: Receptor Activity-Modifying Protein Complexes", Molecular Pharmacology 67(5):1655-1665 (2005).
Howard III M.A. et al., "Intracerebral Drug Delivery in Rats With Lesion-Induced Memory Deficits", J Neurosurg 71:105-112 (Jul. 1989).
Jurgens C.A. et al., "β-Cell Loss and β-Cell Apoptosis in Human Type 2 Diabetes are Related to Islet Amyloid Deposition", The American Journal of Pathology 178(6):2632-2640 (Jun. 2011).
Koda J.E. et al., "Amylin Concentrations and Glucose Control", The Lancet 339:1179-1180 (May 9, 1992).
Koo B.W. et al., "Amide Inequivalence in the Fibrillar Assembly of Islet Amyloid Polypeptide", Protein Engineering, Design & Selection 21(3):147-154 (2008).
Kruger D.F. et al., "Pramlintide for the Treatment of Insulin-Requiring Diabetes Mellitus", Drugs 64(13):1419-1432 (2004).
Langer R., "New Methods of Drug Delivery", New Methods of Drug Delivery 249:1527-1533 (Sep. 28, 1990).
Levy R.J. et al., "Inhibition of Calcification of Bioprosthetic Heart Valves by Local Controlled-Release Diphosphonate", Science 228:190 (Apr. 12, 1985).
Marek P. et al., "Efficient Microwave-Assisted Synthesis of Human Islet Amyloid Polypeptide Designed to Facilitate the Specific Incorporation of Labeled Amino Acids", Organic Letters 12(21):4848-4851 (2010).
Matteucci M.D. et al., "Synthesis of Deoxyoligonucleotides on a Polymer Support", J. Am. Chem. Soc. 103 (11):3185-3191 (1981).
Meng F. et al., "The Combination of Kinetically Selected Inhibitors in Trans Leads to the Highly Effective Inhibition of Amyloid Formation", J Am Chem Soc. 132(41):14340-14342 (Oct. 20, 2010).
Merrifield R.B., "Solid Phase Peptide Synthesis. I. The Synthesis of a Tetrapeptide", J. Am. Chem. Soc. 85:2149-2154 (Jul. 20, 1963).
Montane J. et al., "Metabolic Stress, IAPP and Islet Amyloid", Diabetes, Obesity and Metabolism 14(Suppl 3):68-77 (Oct. 2012).
Potter K.J. et al., "Islet Amyloid Deposition Limits the Viability of Human Islet Grafts But Not Porcine Islet Grafts", PNAS 107(9):4305-4310 (Mar. 2, 2010).
Rushing P.A. et al., "Inhibition of Central Amylin Signaling Increases Food Intake and Body Adiposity in Rats", Endocrinology 142(11):5035-5038 (2001).
Scherbaum W.A. et al, "The Role of Amylin in the Physiology of Glycemic Control", Experimental and Clinical Endocrinology & Diabetes 106:97-102 (1998).
Schmidt M L et al., "Chemical and Immunological Heterogeneity of Fibrillar Amyloid in Plaques of Alzheimer's Disease and Down's Syndrome Brains Revealed by Confocal Microscopy" American Journal of Pathology 147 (2):503-515 (Aug. 1995).
Schnölzer M. et al., "In Situ Neutralization in Boc-Chemistry Solid Phase Peptide Synthesis", Int. J. Peptide Protein Res. 40:180-193 (1992).
Wang H. et al., "Rationally Desighed, Nontoxic, Nonamyloidogenic Analogues of Human Islet Amyloid Polypeptide With Improved Solubility", Biochemistry 53:5876-5884 (2014).
Westermark P. et al., "Islet Amyloid Polypeptide, Islet Amyloid and Diabetes Mellitus", Physiol Rev 91:795-826 (Jul. 2011).
Westermark G.T., "Widespread Amyloid Deposition in Transplanted Human Pancreatic Islets", The New England Journal of Medicine 359(9):977-979 (Aug. 28, 2008).
Westermark P. et al., "Islet Amyloid Polypeptide: Pinpointing Amino Acid Residues Linked to Amyloid Fibril Formation", Proc. Natl. Acad. Sci. USA 87:5036-5040 (Jul. 1990).
Williamson J.A. et al., "Direct Detection of Transient α-Helical States in Islet Amyloid Polypeptide", Protein Science 16:110-117 (2007).
Wu G.Y. et al., "Receptor-Mediated In Vitro Gene Transformation by a Soluble DNA Carrier System", The Journal of Biological Chemistry 262(10):4429-4432 (1987).
GenBank AAA35524.1 (Mar. 1, 1994), 1 page.
The pH Scale from Chemistry LibreText, https://chem.libretexts.org/Brookshelves/General_Chemistry/Map%3A_Chemistry_, pp. 1-7 (2019).
Extended Supplementary European Search Report dated Sep. 8, 2017 received in European Application No. 15 78 6103.0.
European Examination Report dated Dec. 12, 2019 received in European Application No. 15 786 103.0.
International Search Report and Written Opinion dated Jan. 11, 2016 received in International Patent Application No. PCT/US15/28683.
International Search Report dated Jun. 11, 2018 issued in PCT/US2018/016348.

\* cited by examiner

A

B

C

D

E

SEQUENCE LISTING

```
<160> NUMBER OF SEQ ID NOS: 22

<210> SEQ ID NO 1
<211> LENGTH: 37
<212> TYPE: PRT
<213> ORGANISM: Homo sapiens

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 37
<212> TYPE: PRT
<213> ORGANISM: Artificial Sequence
<220> FEATURE:
<223> OTHER INFORMATION: mutant islet amyloid polypeptide with amidated
      c-terminal and proline at positions 25, 28 and 29

<400> SEQUENCE: 2

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 3
<211> LENGTH: 37
<212> TYPE: PRT
<213> ORGANISM: Artificial Sequence
<220> FEATURE:
<223> OTHER INFORMATION: mutant-human islet amyloid polypeptide, amino
      acid substitutions at positions 21 and 35

<400> SEQUENCE: 3
```

```
Lys Cys Asn Thr Ala Thr Cys Ala Thr Gln Arg Leu Ala Asn Phe Leu
1               5                   10                  15

Val His Ser Ser Lys Asn Phe Gly Ala Ile Leu Ser Thr Asn Val
                20                  25                  30

Gly Ser Lys Thr Tyr
            35

<210> SEQ ID NO 4
<211> LENGTH: 37
<212> TYPE: PRT
<213> ORGANISM: Artificial Sequence
<220> FEATURE:
<223> OTHER INFORMATION: mutant-human islet amyloid polypeptide, amino
      acid substitutions at positions 21, 24, 26 and 35

<400> SEQUENCE: 4

Lys Cys Asn Thr Ala Thr Cys Ala Thr Gln Arg Leu Ala Asn Phe Leu
1               5                   10                  15

Val His Ser Ser Lys Asn Phe Pro Ala Pro Leu Ser Ser Thr Asn Val
                20                  25                  30

Gly Ser Lys Thr Tyr
            35

<210> SEQ ID NO 5
<211> LENGTH: 37
<212> TYPE: PRT
<213> ORGANISM: Artificial Sequence
<220> FEATURE:
<223> OTHER INFORMATION: mutant-human islet amyloid polypeptide, amino
      acid substitutions at positions 22 and 31

<400> SEQUENCE: 5

Lys Cys Asn Thr Ala Thr Cys Ala Thr Gln Arg Leu Ala Asn Phe Leu
1               5                   10                  15

Val His Ser Ser Asn Lys Phe Gly Ala Ile Leu Ser Ser Thr Lys Val
                20                  25                  30

Gly Ser Asn Thr Tyr
            35

<210> SEQ ID NO 6
<211> LENGTH: 37
<212> TYPE: PRT
<213> ORGANISM: Artificial Sequence
<220> FEATURE:
<223> OTHER INFORMATION: mutant-human islet amyloid polypeptide, amino
      acid substitutions at positions 22, 24, 26 and 31

<400> SEQUENCE: 6

Lys Cys Asn Thr Ala Thr Cys Ala Thr Gln Arg Leu Ala Asn Phe Leu
1               5                   10                  15

Val His Ser Ser Asn Lys Phe Pro Ala Pro Leu Ser Ser Thr Lys Val
                20                  25                  30

Gly Ser Asn Thr Tyr
            35

<210> SEQ ID NO 7
<211> LENGTH: 37
<212> TYPE: PRT
<213> ORGANISM: Artificial Sequence
<220> FEATURE:
<223> OTHER INFORMATION: mutant-human islet amyloid polypeptide, with
      amidated c-terminal and amino acid substitutions at positions 21
      and 35
<220> FEATURE:
```

```
<221> NAME/KEY: MOD_RES
<222> LOCATION: (37)..(37)
<223> OTHER INFORMATION: AMIDATION

<400> SEQUENCE: 7

Lys Cys Asn Thr Ala Thr Cys Ala Thr Gln Arg Leu Ala Asn Phe Leu
1               5                   10                  15

Val His Ser Ser Lys Asn Phe Gly Ala Ile Leu Ser Ser Thr Asn Val
            20                  25                  30

Gly Ser Lys Thr Tyr
        35

<210> SEQ ID NO 8
<211> LENGTH: 37
<212> TYPE: PRT
<213> ORGANISM: Artificial Sequence
<220> FEATURE:
<223> OTHER INFORMATION: mutant-human islet amyloid polypeptide, with
      amidated c-terminal and amino acid substitutions at positions 21,
      24, 26 and 35
<220> FEATURE:
<221> NAME/KEY: MOD_RES
<222> LOCATION: (37)..(37)
<223> OTHER INFORMATION: AMIDATION

<400> SEQUENCE: 8

Lys Cys Asn Thr Ala Thr Cys Ala Thr Gln Arg Leu Ala Asn Phe Leu
1               5                   10                  15

Val His Ser Ser Lys Asn Phe Pro Ala Pro Leu Ser Ser Thr Asn Val
            20                  25                  30

Gly Ser Lys Thr Tyr
        35

<210> SEQ ID NO 9
<211> LENGTH: 37
<212> TYPE: PRT
<213> ORGANISM: Artificial Sequence
<220> FEATURE:
<223> OTHER INFORMATION: mutant-human islet amyloid polypeptide, with
      amidated c-terminal and amino acid substitutions at positions 22
      and 31
<220> FEATURE:
<221> NAME/KEY: MOD_RES
<222> LOCATION: (37)..(37)
<223> OTHER INFORMATION: AMIDATION

<400> SEQUENCE: 9

Lys Cys Asn Thr Ala Thr Cys Ala Thr Gln Arg Leu Ala Asn Phe Leu
1               5                   10                  15

Val His Ser Ser Asn Lys Phe Gly Ala Ile Leu Ser Ser Thr Lys Val
            20                  25                  30

Gly Ser Asn Thr Tyr
        35

<210> SEQ ID NO 10
<211> LENGTH: 37
<212> TYPE: PRT
<213> ORGANISM: Artificial Sequence
<220> FEATURE:
<223> OTHER INFORMATION: mutant-human islet amyloid polypeptide, with
      amidated c-terminal and amino acid substitutions at positions 22,
      24, 26 and 31
<220> FEATURE:
<221> NAME/KEY: MOD_RES
<222> LOCATION: (37)..(37)
<223> OTHER INFORMATION: AMIDATION
```

```
<400> SEQUENCE: 10

Lys Cys Asn Thr Ala Thr Cys Ala Thr Gln Arg Leu Ala Asn Phe Leu
1               5                   10                  15

Val His Ser Ser Asn Lys Phe Pro Ala Pro Leu Ser Ser Thr Lys Val
            20                  25                  30

Gly Ser Asn Thr Tyr
        35

<210> SEQ ID NO 11
<211> LENGTH: 37
<212> TYPE: PRT
<213> ORGANISM: Artificial Sequence
<220> FEATURE:
<223> OTHER INFORMATION: mutant-human islet amyloid polypeptide, amino
      acid substitutions at positions 21, 24 and 35

<400> SEQUENCE: 11

Lys Cys Asn Thr Ala Thr Cys Ala Thr Gln Arg Leu Ala Asn Phe Leu
1               5                   10                  15

Val His Ser Ser Lys Asn Phe Pro Ala Ile Leu Ser Ser Thr Asn Val
            20                  25                  30

Gly Ser Lys Thr Tyr
        35

<210> SEQ ID NO 12
<211> LENGTH: 37
<212> TYPE: PRT
<213> ORGANISM: Artificial Sequence
<220> FEATURE:
<223> OTHER INFORMATION: mutant-human islet amyloid polypeptide, amino
      acid substitutions at positions 21, 26 and 35

<400> SEQUENCE: 12

Lys Cys Asn Thr Ala Thr Cys Ala Thr Gln Arg Leu Ala Asn Phe Leu
1               5                   10                  15

Val His Ser Ser Lys Asn Phe Gly Ala Pro Leu Ser Ser Thr Asn Val
            20                  25                  30

Gly Ser Lys Thr Tyr
        35

<210> SEQ ID NO 13
<211> LENGTH: 37
<212> TYPE: PRT
<213> ORGANISM: Artificial Sequence
<220> FEATURE:
<223> OTHER INFORMATION: mutant-human islet amyloid polypeptide, amino
      acid substitutions at positions 22, 24 and 31

<400> SEQUENCE: 13

Lys Cys Asn Thr Ala Thr Cys Ala Thr Gln Arg Leu Ala Asn Phe Leu
1               5                   10                  15

Val His Ser Ser Asn Lys Phe Pro Ala Ile Leu Ser Ser Thr Lys Val
            20                  25                  30

Gly Ser Asn Thr Tyr
        35

<210> SEQ ID NO 14
<211> LENGTH: 37
<212> TYPE: PRT
<213> ORGANISM: Artificial Sequence
<220> FEATURE:
<223> OTHER INFORMATION: mutant-human islet amyloid polypeptide, amino
      acid substitutions at positions 22, 26 and 31
```

<400> SEQUENCE: 14

Lys Cys Asn Thr Ala Thr Cys Ala Thr Gln Arg Leu Ala Asn Phe Leu
1               5                   10                  15

Val His Ser Ser Asn Lys Phe Gly Ala Pro Leu Ser Ser Thr Lys Val
            20                  25                  30

Gly Ser Asn Thr Tyr
        35

<210> SEQ ID NO 15
<211> LENGTH: 37
<212> TYPE: PRT
<213> ORGANISM: Artificial Sequence
<220> FEATURE:
<223> OTHER INFORMATION: mutant-human islet amyloid polypeptide, amino
      acid substitutions at positions 21, 28 and 35

<400> SEQUENCE: 15

Lys Cys Asn Thr Ala Thr Cys Ala Thr Gln Arg Leu Ala Asn Phe Leu
1               5                   10                  15

Val His Ser Ser Lys Asn Phe Gly Ala Ile Leu Pro Ser Thr Asn Val
            20                  25                  30

Gly Ser Lys Thr Tyr
        35

<210> SEQ ID NO 16
<211> LENGTH: 37
<212> TYPE: PRT
<213> ORGANISM: Artificial Sequence
<220> FEATURE:
<223> OTHER INFORMATION: mutant-human islet amyloid polypeptide, amino
      acid substitutions at positions 22, 28 and 31

<400> SEQUENCE: 16

Lys Cys Asn Thr Ala Thr Cys Ala Thr Gln Arg Leu Ala Asn Phe Leu
1               5                   10                  15

Val His Ser Ser Asn Lys Phe Gly Ala Ile Leu Pro Ser Thr Lys Val
            20                  25                  30

Gly Ser Asn Thr Tyr
        35

<210> SEQ ID NO 17
<211> LENGTH: 37
<212> TYPE: PRT
<213> ORGANISM: Artificial Sequence
<220> FEATURE:
<223> OTHER INFORMATION: mutant-human islet amyloid polypeptide with
      amidated c-terminal, amino acid substitutions at positions 21, 24
      and 35
<220> FEATURE:
<221> NAME/KEY: MOD_RES
<222> LOCATION: (37)..(37)
<223> OTHER INFORMATION: amidation

<400> SEQUENCE: 17

Lys Cys Asn Thr Ala Thr Cys Ala Thr Gln Arg Leu Ala Asn Phe Leu
1               5                   10                  15

Val His Ser Ser Lys Asn Phe Pro Ala Ile Leu Ser Ser Thr Asn Val
            20                  25                  30

Gly Ser Lys Thr Tyr
        35

<210> SEQ ID NO 18

```
<211> LENGTH: 37
<212> TYPE: PRT
<213> ORGANISM: Artificial Sequence
<220> FEATURE:
<223> OTHER INFORMATION: mutant-human islet amyloid polypeptide with
      amidated C-terminus, amino acid substitutions at positions 21, 26
      and 35
<220> FEATURE:
<221> NAME/KEY: MOD_RES
<222> LOCATION: (37)..(37)
<223> OTHER INFORMATION: amidation

<400> SEQUENCE: 18

Lys Cys Asn Thr Ala Thr Cys Ala Thr Gln Arg Leu Ala Asn Phe Leu
1               5                   10                  15

Val His Ser Ser Lys Asn Phe Gly Ala Pro Leu Ser Ser Thr Asn Val
            20                  25                  30

Gly Ser Lys Thr Tyr
            35

<210> SEQ ID NO 19
<211> LENGTH: 37
<212> TYPE: PRT
<213> ORGANISM: Artificial Sequence
<220> FEATURE:
<223> OTHER INFORMATION: mutant-human islet amyloid polypeptide with an
      amidated c-terminus, amino acid substitutions at positions 21, 28
      and 35
<220> FEATURE:
<221> NAME/KEY: MOD_RES
<222> LOCATION: (37)..(37)
<223> OTHER INFORMATION: amidation

<400> SEQUENCE: 19

Lys Cys Asn Thr Ala Thr Cys Ala Thr Gln Arg Leu Ala Asn Phe Leu
1               5                   10                  15

Val His Ser Ser Lys Asn Phe Gly Ala Ile Leu Pro Ser Thr Asn Val
            20                  25                  30

Gly Ser Lys Thr Tyr
            35

<210> SEQ ID NO 20
<211> LENGTH: 37
<212> TYPE: PRT
<213> ORGANISM: Artificial Sequence
<220> FEATURE:
<223> OTHER INFORMATION: mutant-human islet amyloid polypeptide with an
      amidated c-terminus, amino acid substitutions at positions 22, 24
      and 31
<220> FEATURE:
<221> NAME/KEY: MOD_RES
<222> LOCATION: (37)..(37)
<223> OTHER INFORMATION: amidation

<400> SEQUENCE: 20

Lys Cys Asn Thr Ala Thr Cys Ala Thr Gln Arg Leu Ala Asn Phe Leu
1               5                   10                  15

Val His Ser Ser Asn Lys Phe Pro Ala Ile Leu Ser Ser Thr Lys Val
            20                  25                  30

Gly Ser Asn Thr Tyr
            35

<210> SEQ ID NO 21
<211> LENGTH: 37
<212> TYPE: PRT
<213> ORGANISM: Artificial Sequence
<220> FEATURE:
```

```
<223> OTHER INFORMATION: mutant-human islet amyloid polypeptide with an
      amidated c-terminus, amino acid substitutions at positions 22, 26
      and 31
<220> FEATURE:
<221> NAME/KEY: MOD_RES
<222> LOCATION: (37)..(37)
<223> OTHER INFORMATION: amidation

<400> SEQUENCE: 21

Lys Cys Asn Thr Ala Thr Cys Ala Thr Gln Arg Leu Ala Asn Phe Leu
1               5                   10                  15

Val His Ser Ser Asn Lys Phe Gly Ala Pro Leu Ser Ser Thr Lys Val
                20                  25                  30

Gly Ser Asn Thr Tyr
            35

<210> SEQ ID NO 22
<211> LENGTH: 37
<212> TYPE: PRT
<213> ORGANISM: Artificial Sequence
<220> FEATURE:
<223> OTHER INFORMATION: mutant-human islet amyloid polypeptide with an
      amidated c-terminus, amino acid substitutions at positions 22, 28
      and 31
<220> FEATURE:
<221> NAME/KEY: MOD_RES
<222> LOCATION: (37)..(37)
<223> OTHER INFORMATION: amidation

<400> SEQUENCE: 22

Lys Cys Asn Thr Ala Thr Cys Ala Thr Gln Arg Leu Ala Asn Phe Leu
1               5                   10                  15

Val His Ser Ser Asn Lys Phe Gly Ala Ile Leu Pro Ser Thr Lys Val
                20                  25                  30

Gly Ser Asn Thr Tyr
            35
```

MUTANT ISLET AMYLOID POLYPEPTIDES WITH IMPROVED SOLUBILITY AND METHODS FOR USING THE SAME

CROSS REFERENCE TO RELATED APPLICATION

This application claims the benefit of priority from PCT International Application No. PCT/US2018/016348 filed Feb. 1, 2018, which claims the benefit of U.S. Provisional Application No. 62/453,068, filed on Feb. 1, 2017, the entire contents of each of which is incorporated herein by reference.

STATEMENT REGARDING FEDERALLY SPONSORED RESEARCH

This invention was made with government support under grant number GM078114 awarded by the National Institutes of Health. The government has certain rights in the invention.

INCORPORATION BY REFERENCE OF SEQUENCE LISTING

The Sequence Listing in the ASCII text file, named as R8857_US_SequenceListing.txt of 13 KB, created on Jul. 30, 2019 and submitted to the United States Patent and Trademark Office via EFS-Web, is incorporated herein by reference.

FIELD OF THE DISCLOSURE

This disclosure relates generally, to the design, generation and isolation of, modified human islet amyloid polypeptides (hIAPP, also known as human amylin or amylin). Specifically, the present disclosure provides mutant-hIAPP polypeptides that are soluble at physiological pH and more soluble that wild-type hIAPP, as well as existing modified hIAPP therapeutic peptides. Further, the specific mutant-hIAPP polypeptides of the present disclosure do not aggregate or form amyloid fibrils, and thus are non-toxic to cells when compared to endogenous hIAPP. The instant disclosure also provides methods for using the mutant-hIAPP polypeptides of the present disclosure to treat various pathologies such as, for example, amyloid-based diseases (e.g., type-2 diabetes, amyloidoses) and non-amyloid conditions such as, for example, type-1 diabetes.

BACKGROUND OF THE DISCLOSURE

β-cell death and dysfunction play central roles in the progression of type-2 diabetes and pancreatic islet amyloid formation by the polypeptide hormone amylin (islet amyloid polypeptide, IAPP) is an important contributing factor. See, e.g., Montane, J., et al. *Diabetes Obes. Metab.* (2012) Vol. 14 Suppl. 3, pp. 68-77; and Cao, P., et al. *FEBS Lett.* (2013) Vol. 587, pp. 1106-1118. Human islet amyloid polypeptide (hIAPP or amylin) is a neuroendocrine hormone produced in the pancreatic β-cells, which is stored in the insulin secretory granule and co-secreted with insulin. See Cooper, G. J. et al., *Proc. Natl. Acad. Sci.* (1987) Vol. 84 pp. 8628-8632; and Clark, A. et al., *Lancet* (1987) Vol. 2, pp. 231-234. In type-1 diabetes, the insulin and IAPP producing pancreatic β-cells are destroyed leading to a lack of these hormones. Insulin therapy is the most widely used clinical treatment for diabetes. Despite improvements in insulin therapy over the past few decades, the goal of reinstating complete physiological glucose homeostasis in diabetes patients have not been achieved. In particular, postprandial hyperglycemia remains an obstacle even with aggressive insulin therapy; in part because diabetes is a multihormonal disease, which involves the disturbed secretion of several hormones that physiologically, work in synergy to achieve normal glycemic control. See Kruger et al., *Drugs* (2004) 64 pp. 1419-1432.

In non-diabetic subjects, hIAPP complements the effects of insulin in postprandial glycemic control by suppressing glucagon secretion, and by helping regulate the rate of gastric emptying, and by inducing satiety to suppress food intake. See Scherbaum, W. A., *Exp. Clin. Endocr. Diab.* (1998) Vol. 106, pp. 97-102; and Rushing, P. A. et al., *Endocrinology* (2001) Vol. 142, pp. 5035-5038. However, in type-2 diabetic subjects the deposition of islet amyloid contributes to pancreatic β-cell dysfunction and β-cell death. The deposition of islet amyloid is also a major contributor to the failure of islet transplants and is one of the factors that limit the potential of this therapeutic approach for the treatment of type-1 and type-2 diabetes. IAPP is absent in type-1 diabetes. See Westermark, G. T., et al. *N. Engl. J. Med.* (2008) Vol. 359, pp. 977-979; Potter, K. J., et al. *Proc. Natl Acad. Sci.* (2010) Vol. 107, pp. 4305-4310; Westermark, P., et al. *Physiol. Rev.* (2011) Vol. 91, pp. 795-826; Akter, R. et al. *J. Diabetes Res.* (2016), Article 2798269; and Abedini, A., and Schmidt, A. M. *FEBS Lett.* (2013) 587, pp. 1119-1127.

Even though hIAPP is deficient in both type-1 and type-2 diabetes patients (see Koda, J. E. et al., *Lancet* (1992) Vol. 339, pp. 1179-1180), clinical use of hIAPP has been impractical because of hIAPP's aggressive tendency to aggregate, which causes difficulties in formulation and storage. Furthermore, hIAPP aggregates are toxic to cells. Westermark, P., et al. *Physiol. Rev.* (2011) Vol. 91, pp. 795-826.

Recently certain soluble analogs of hIAPP have been developed, such as those set forth in PCT/US2015/028683 to Raleigh et al., as well as pramlintide, i.e., Symlin™, which has been approved by the FDA. However, a major limitation on presently approved pramlintide is that pramlintide has very limited solubility at physiological pH. See Kruger et al., *Drugs* (2004) Vol. 64, pp. 1419-1432. For example, wild-type hIAPP and pramlintide are soluble at acidic (i.e., pH of about 4.0), whereas certain insulin based treatments, i.e., Humalog®, Apidra®, NovoLog®, Humulin®, Novolin®, Levemir® are formulated at neutral pH (i.e., pH 7.0-7.8). As such, co-formulation of Symlin™ with insulin is not possible, which results in separate injections of both therapeutic agents. The novel mutant-hIAPP polypeptides described herein address this issue, remain bioactive and are uniquely soluble at physiological pH.

To date, hIAPP solubility and the development of soluble analogs for the treatment of human disease has generally focused on replacement of residues in hIAPP with the proline residues found in rat IAPP at positions 25, 28 and 29 substituted into hIAPP and other modified hIAPP proteins containing proline substitutions with the addition of a single charged residue. See PCT/US2015/028683; and Abedini, A., and Raleigh, D. P. *J. Mol. Biol.* (2006) Vol. 355, pp. 274-281. Notably, attempts to analyze the effects of certain single Asparagine substitutions in amylin have been confusing and unpredictable. See Koo, B. W., et al., *Protein Eng., Design & Selection* (2008) Vol. 21:3, pp. 147-154. For example, Koo et al., studied a truncated form of IAPP comprised of residues 8 to 37 and states that certain Asparagine substitutions (N14, N21, N22) aggregate aggressively and do not significantly alter the ability of amylin to form amyloid (N31, N35), while other Asparagine mutations slowed amyloid formation only moderately. Taken together, these data lead Koo et al. (2008), to conclude that amylin is generally unaltered by mutation of Asparagine residues between amino acids 8-37 of the hIAPP protein, regardless of which Asparagine residues are removed or whether Proline residues are added. See Discussion of Koo et. al. (2008). Contrary to the teaching of Koo et al. (2008), the present disclosure shows that substitution of certain Asparagine residues in combination with either certain Proline substitutions or additional Asparagine residue substitutions increase amylin solubility at neutral pH and prevents amyloid formation, when compared to that of the wild-type hIAPP protein.

SUMMARY OF THE DISCLOSURE

Wild-type, mature hIAPP is composed of 37 amino acid residues with an amidated C-terminus and a disulfide bond between Cys-2 and Cys-7 (see FIG. 1, SEQ ID NO: 1). The wild-type polypeptide is soluble at acidic pH, has very limited solubility at neutral pH and is highly amyloidogenic under physiological conditions. Aggregates formed by the in vitro aggregation of hIAPP are toxic to pancreatic beta-cells and islets and amyloid formation in vivo leads to pancreatic beta-cell death. See Westermark, P., et al. *Physiol. Rev.* (2011) Vol. 91, pp. 795-826.

Without being bound by any one particular theory, the inventors have identified that substitution of certain amino acids within the wild-type human IAPP amino acid sequence results in improved polypeptide solubility at neutral pH when compared to wild-type hIAPP and other modified hIAPP proteins, such as existing Food and Drug Administration (FDA) approved pramlintide, i.e., Symlin™ (SEQ ID NO: 2). The present disclosure also reveals, for the first time, that amino acid substitutions in the wild-type human hIAPP amino acid sequence prevent amlyoid formation, are able to be co-formulated with insulin (e.g., existing therapeutic insulin formulations) at neutral pH, while retaining the ability to bind human calcitonin and human amylin receptors. As such, the present disclosure provides novel compositions and therapeutic methods of using the same.

In a first aspect of the present disclosure, analogs of hIAPP polypeptides (mutant-hIAPP polypeptides) are provided, which exhibit increased solubility over that of the wild-type hIAPP polypeptide and existing modified hIAPP therapeutic peptides such as pramlintide, i.e., Symlin™ (SEQ ID NO: 2) at neutral pH. Further, the soluble, mutant hIAPP polypeptides of the present disclosure are non-toxic to β-cells, do not form harmful amyloid fibrils (i.e., fail to aggregate), and retain their natural ability to modulate human calcitonin receptor and human amylin receptor.

In one embodiment, mutant-hIAPP polypeptides are provided that, when compared to the wild-type hIAPP amino acid sequence of SEQ ID NO: 1, include an amino acid substitution in at least one of the following positions: 21, 22, 31 and 35. In other embodiments, when compared to the wild-type hIAPP amino acid sequence, the mutant-hIAPP polypeptides of the instant disclosure include an amino acid substitution in at least two of the following positions: 21, 22, 31 and 35. In yet other embodiments, the mutant-hIAPP polypeptides of the instant disclosure include an amino acid substitution in at least three of the following positions: 21, 22, 31 and 35, when compared to the wild-type hIAPP amino acid sequence. In another instance, the mutant-hIAPP polypeptide of the instant disclosure includes an amino acid substitution at each of the following positions: 21, 22, 31 and 35, when compared to the wild-type hIAPP amino acid sequence.

In certain embodiments, the mutant-hIAPP polypeptides of the present disclosure contain an amino acid substitution from Asparagine to Lysine and/or Asparagine to Arginine at one or more of the following positions: 21, 22, 31 and 35. In some embodiments, the mutant-hIAPP polypeptide of the present disclosure has an amino acid substitution from Asparagine to Lysine and/or Asparagine to Arginine at two or three of the following positions: 21, 22, 31 and 35. In another embodiment, the mutant-hIAPP polypeptide has an amino acid substitution from Asparagine to Lysine or Asparagine to Arginine at all four of the following positions: 21, 22, 31 and 35.

In specific embodiments, the mutant-hIAPP polypeptides of the present disclosure have an amino acid substitution from Asparagine to Lysine at one, two or three of the following positions: 21, 22, 31 and 35, relative to the wild-type hIAPP amino acid sequence. In another embodiment, the mutant-hIAPP polypeptide disclosure contains an amino acid substitution from Asparagine to Lysine at all of the following positions: 21, 22, 31 and 35.

For example, in one embodiment, the mutant-hIAPP polypeptide includes an Asparagine to Lysine substitution at at least positions 21 and 35 of the wild-type hIAPP peptide sequence. In another embodiment, the mutant-hIAPP polypeptide includes an Asparagine to Lysine substitution at at least positions 22 and 31 of the wild-type hIAPP peptide sequence. In a specific embodiment, the mutant-hIAPP polypeptide contains only an Asparagine to Lysine substitution at positions 21 and 35 of the wild-type hIAPP peptide sequence, as set forth in SEQ ID NOs: 3 or 7.

In other embodiments of the present disclosure, the mutant-hIAPP polypeptides of the present disclosure can include at least one amino acid substitution at position 21, 22, 31 and 35, as well as at least one amino acid substitution at position 24 and 26. In other embodiments, the mutant-hIAPP polypeptide includes at least one amino acid substitution at position 21, 22, 31 and 35, as well as at least one Proline substitution at positions 24, 26 and 28. In yet another embodiment, the mutant-hIAPP polypeptides of the present disclosure include Proline substitutions at positions 24 and 26 relative to wild-type hIAPP, i.e., G24P and I26P substitutions. In certain embodiments, the amino acid substitutions at positions 24 and/or 26 include N-Methyl Glycine at position 24, N-Methyl Isoleucine at position 26 and/or N-Methyl Serine at position 28.

Other embodiments of the present disclosure include mutant-hIAPP polypeptides of the including amino acid substitutions at positions 21 and 31 and a single Proline residue substitution at one of positions 24, 26 or 28. In certain embodiments, mutant-hIAPP polypeptides of the present disclosure include amino acid substitutions at positions 22 and 35 and a single Proline residue substitution at one of positions 24, 26 or 28. In yet another embodiment, mutant-hIAPP polypeptides of the present disclosure include amino acid substitutions at positions 21 and 22 and a single Proline residue substitution at one of positions 24, 26 or 28. In another embodiment, mutant-hIAPP polypeptides of the present disclosure include amino acid substitutions at positions 31 and 35, and a single Proline residue substitution at one of positions 24, 26 or 28. In specific embodiments, the mutant-hIAPP polypeptides contain an amino acid substitution at positions 21, 22, 31 and/or 35 from Asparagine to Lysine. Asparagine to Arginine or Asparagine to Ornithine, and a single Proline residue substitution at any one of positions 24, 26 or 28.

In certain embodiments, when compared to the wild-type-hIAPP peptide of SEQ ID NO: 1 the mutant-hIAPP polypeptide comprises amino acid substitutions, N21K and N35K, as set forth in SEQ ID NOs. 3, 4, 7 and 8. In one instance, when compared to the wild-type-hIAPP peptide of SEQ ID NO: 1 the mutant-hIAPP polypeptide comprises the following amino acid substitutions: N21K, G24P, I26P and N35K, as set forth in SEQ ID NOs: 4 and 8.

In other exemplary embodiments, when compared to the wild-type-hIAPP peptide of SEQ ID NO: 1, the mutant-hIAPP polypeptide comprises amino acid substitutions, N22K and N31K as set forth in SEQ ID NOs: 5, 6, 9, 10, 16 and 22. For example, in one instance, the mutant-hIAPP polypeptide includes all of the following amino acid substitutions: N22K, G24P, I26P and N31K, as set forth in SEQ ID NOs 6 and 10. In another example, when compared to the wild-type-hIAPP peptide the mutant-hIAPP polypeptide includes all of the following amino acid substitutions: N22K, S28P and N31K, as set forth in SEQ ID NOs: 16 and 22.

As stated above, the present disclosure unexpectedly reveals that certain amino acid substitutions in the wild-type human hIAPP confer hIAPP with the ability to be formulated at neutral pH with or without insulin (e.g., existing therapeutic insulin formulations), while retaining the ability to bind human calcitonin and human amylin receptors.

Therefore, in another aspect, the mutant-hIAPP polypeptides of the present disclosure are formulated in a neutral solution (i.e., physiological pH or pH 7.0-7.8).

In certain embodiments, one or more of the mutant-hIAPP polypeptides of the present disclosure are formulated as a pharmacological composition at neutral pH. In one embodiment the neutral pharmacological formulation includes at least two mutant-hIAPP polypeptides of the present disclosure. In another embodiment, the neutral pharmacological formulation is a solution that includes at least two different mutant-hIAPP polypeptides of the present disclosure. In yet another embodiment, the neutral pharmacological formulation is a solution that includes at least three different mutant-hIAPP polypeptides of the present disclosure. In one instance, the neutral pharmacological formulation is a solution that includes a plurality (i.e., more than 3) of different mutant-hIAPP polypeptides of the present disclosure.

In some instances, the neutral pharmacological formulation of the present disclosure has a pH of between 6.7 and 7.8, between 7.0 and 7.8, between 7.2 and 7.6 or between 7.3 and 7.5. In an exemplary embodiment, the neutral pharmacological formulation is a solution that includes at least one mutant-hIAPP polypeptide of the present disclosure and has a pH of 7.4.

In other embodiments, the neutral pharmacological formulation of the present disclosure includes at least one mutant-hIAPP polypeptide and at least one other therapeutic agent. For example, a neutral pharmacological formulation is a solution that has a pH of between 6.7 and 7.8, between 7.0 and 7.8, between 7.2 and 7.6 or between 7.3 and 7.5, and includes at least one mutant-hIAPP polypeptide and at least one other therapeutic agent, such as insulin.

In certain embodiments the neutral pharmacological formulation includes insulin or synthetic insulin. In a specific instance the synthetic insulin is Humalog®, Apidra®, NovoLog®, Humulin®, Novolin®, Novolin-N®, Levemir® or combinations thereof.

Since the inventors have shown that the mutant-hIAPP polypeptides prevent amlyoid formation and are able to be formulated or co-formulated with insulin (e.g., existing therapeutic insulin formulations) at neutral pH, the neutral pharmacological compositions and mutant-hIAPP proteins of the present disclosure can be used in certain therapeutic methods.

As such, in another aspect of the present disclosure, the mutant-hIAPP polypeptide compositions disclosed herein are administered to a subject for the treatment of an amyloid-based disease, hyperglycemia and/or type-1 diabetes.

In one embodiment, the mutant polypeptide compositions are administered as part of a neutral pharmacological formulation. In some embodiments, the mutant-hIAPP polypeptide compositions of the present disclosure are co-formulated at neutral pH with at least one other therapeutic agent (e.g., insulin, Humalog®, Apidra®, NovoLog®, Humulin®, Novolin®, Novolin-N®, Levemir® or combinations thereof) and administered to a subject for the treatment of an amyloid-based disease. In certain embodiments, the mutant hIAPP polypeptides of the instant disclosure are co-formulated at a neutral pH with a natural insulin or synthetic insulin and administered to a subject having an amyloid-based disease, such as type-2 diabetes or amyloidoses. In another embodiment, the mutant-hIAPP polypeptides of the instant disclosure are co-formulated at a neutral pH with an insulin and provided to a subject having type-1 diabetes or hyperglycemia.

In some embodiments, the mutant polypeptide compositions or neutral formulations thereof are solutions that can be administered to a subject by injection. In certain embodiments, the mutant polypeptide compositions or neutral formulations thereof are administered to a subject by intravenous injection, intraperitoneal injection, intramuscular injection, subcutaneous injection, or a combination thereof.

In certain instances, the mutant polypeptide compositions or neutral formulations thereof can be administered to a subject once a day, twice a day or more often. In some embodiments, the mutant polypeptide compositions or neutral formulations thereof are administered to a subject once a week, twice a week, three times a week, four times a week, 5 times a week, 6 times a week or more. In one embodiment, the mutant polypeptide compositions or neutral formulations thereof are administered to a subject by a pump, such as a portable infusion pump that can deliver a controlled or bolus amount of mutant polypeptide composition to a subject.

In other embodiments, the methods for treatment include measuring one or more of the following in a subject: (a) an increase or decrease in the proliferation, growth, and/or differentiation of cells or the products of cells (such as pancreatic β cells, or the hormones produced in pancreatic β cells) whether those products accumulate within cells or are released therefrom, balancing blood glucose levels and gylcosylated hemoglobin levels; (b) enhancement or reduction of the function of an affected cell or population of cells e.g., glycemic control, reducing amyloid deposits, which are formed in the islets of Langerhans of diabetic subjects are associated with reduced β-cell mass.

BRIEF DESCRIPTION OF DRAWINGS AND TABLES

FIG. 1. Sequence of human-IAPP, and exemplary mutant-hIAPP polypeptides of the present disclosure. Each polypeptide has a disulfide bond connecting Cys 2 and Cys 7 and an amidated C-terminus. Amino acid sequences for wild-type human IAPP as set forth in SEQ ID NO: 1 compared to numerous exemplary mutant-hIAPP polypeptides of the present disclosure. Mutated amino acid residues, which differ from that of wild-type human IAPP are underlined. Exemplary mutant-analog 1 includes the following amino acid residue changes when compared to the wild-type human-IAPP (hIAPP): N22K, G24P, I26P and N31K as set forth in SEQ ID NO: 10. Exemplary mutant-analog 2 includes the following amino acid residue changes when compared to wild-type hIAPP: N21K, G24P, I26P and N35K as set forth in SEQ ID NO: 8. Exemplary mutant-analog 3 includes the following amino acid residue changes when compared to wild-type hIAPP: N21K and N35K as set forth in SEQ ID NO: 7. Exemplary mutant-analog 4 includes the following amino acid residue changes when compared to wild-type hIAPP: N22K, S28P and N35K as set forth in SEQ ID NO: 22.

FIGS. 2A-2D. The kinetics of amyloid formation by wild-type hIAPP compared to exemplary mutant-hIAPP polypeptides as monitored by thioflavin-T fluorescence assays. Thioflavin-T is a small dye that experiences an increase in quantum yield upon binding to amyloid fibrils, and does not alter the kinetics of hIAPP based amyloid formation. (A) The kinetics of amyloid formation of wild-type hIAPP polypeptides compared to exemplary mutant-hIAPP polypeptide analog 1 after 1 week (top) and 6 week (bottom) incubations. (B) The kinetics of amyloid formation of wild-type hIAPP polypeptides compared to exemplary mutant-hIAPP polypeptide analog 2 after 1 week (top) and 6 week (bottom) incubations. (C) The kinetics of amyloid formation of wild-type hIAPP polypeptides compared to exemplary mutant-hIAPP polypeptide analog 3 after 1 week (top) and 6 week (bottom) incubations. (D) The kinetics of amyloid formation of wild-type hIAPP polypeptides compared to exemplary mutant-hIAPP polypeptide analog 4 after 1 week (top) and 6 week (bottom) incubations. The data reveal that none of the mutant hIAPP polypeptides forms amyloid. In contrast, the wild-type hIAPP protein forms significant amounts of amyloid during both time courses. The kinetic experiments were conducted in 10 mM PBS buffer (pH 7.4) without stirring at 25° C. The concentration of wild-type hIAPP and mutant-hIAPP was 16 µM, while the concentration of thioflavin-T was 32 µM for all experiments.

FIGS. 3A-3E. TEM images showing the morphology of any amyloid aggregates that formed. Transmission electron microscopy (TEM) images were obtained after 7 days of incubation, i.e., at the end of each kinetic experiment shown in FIGS. 2A-D (top panels). (A) The wild-type hIAPP samples contain extensive amounts of amyloid fibers. In contrast, no aggregates are observed in the TEM images of the exemplary mutant hIAPP analog 1 (B), mutant analog 2 (C), mutant analog 3 (D) or mutant analog 4 (E). Scale bars represent 100 nm.

Figure 4:
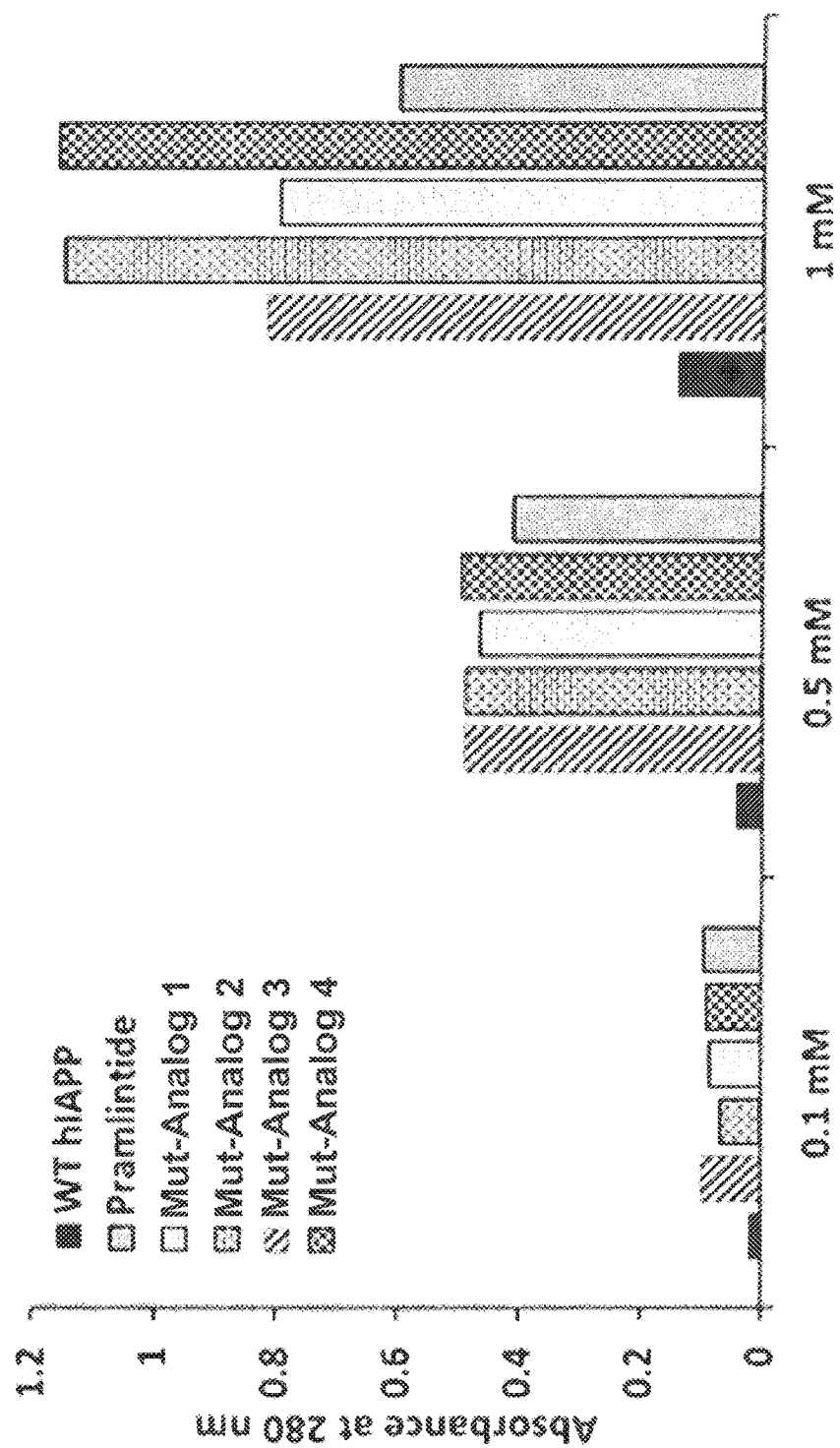
Figures 5A, 5B:
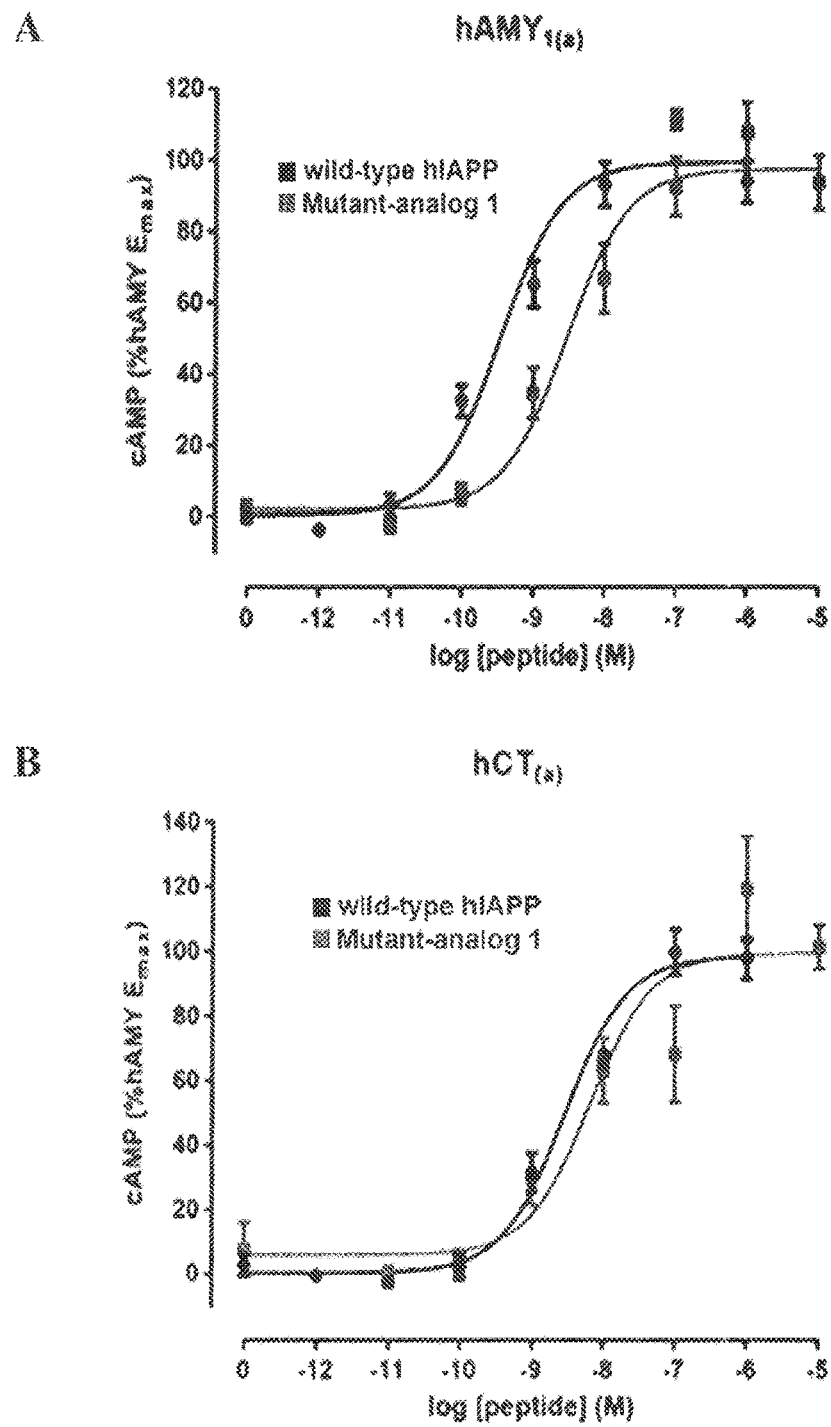
Figure 5C:
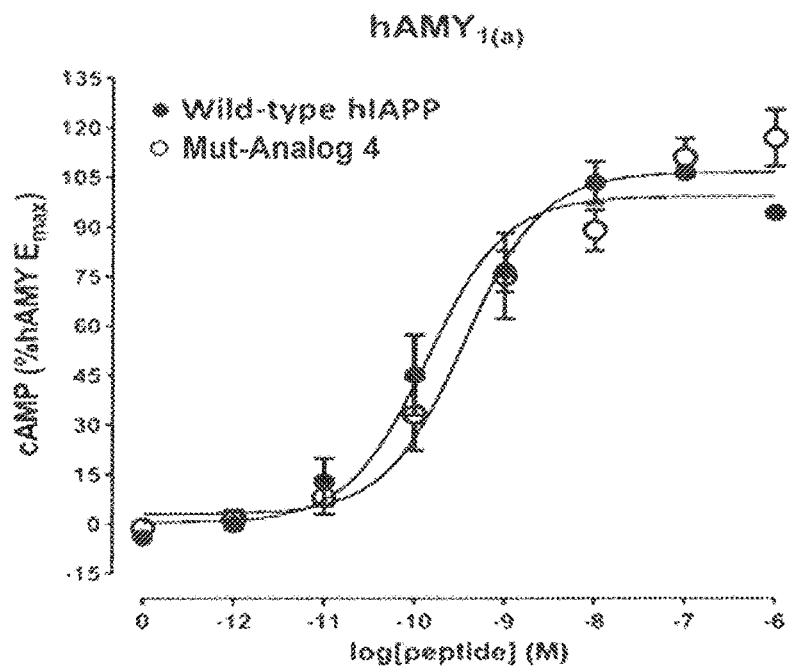
Figure 5D:
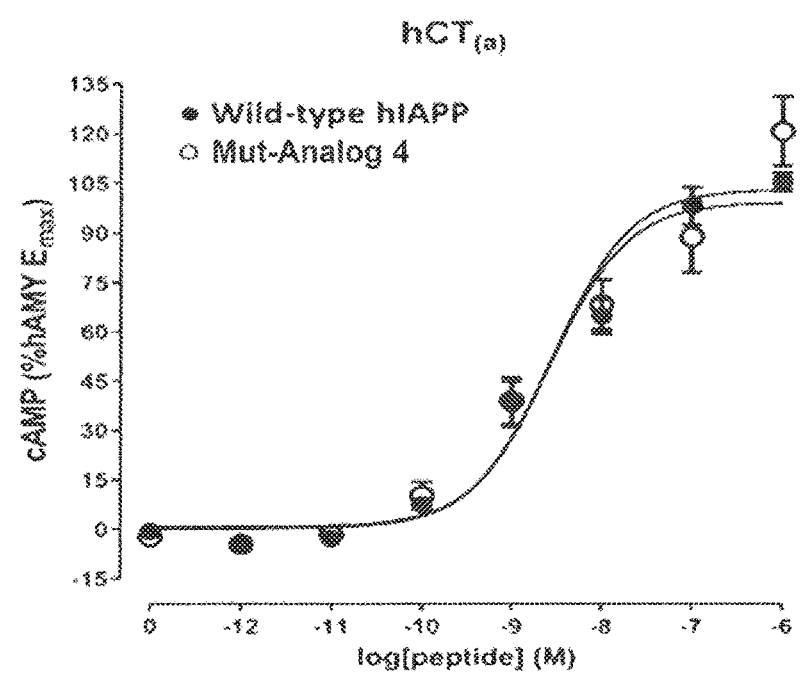

FIG. 4. Comparison of the solubility of exemplary mutant-hIAPP polypeptides and wild-type hIAPP at neutral pH. The solubility of wild-type hIAPP formulated in a neutral solution compared to exemplary mutant-hIAPP polypeptides of the present disclosure. The histogram shows all of the exemplary mutant hIAPP polypeptides (mutant analog 1, SEQ ID NO: 10; mutant analog 2, SEQ ID NO: 8; mutant analog 3, SEQ ID NO: 7; and mutant analog 4, SEQ ID NO: 22) tested are more substantially soluble than wild-type hIAPP (SEQ ID NO: 1) and an existing FDA approved hIAPP polypeptide (e.g., paramlintide (SEQ ID NO: 2). Three sets of experiments were performed at different initial peptide concentrations (0.1, 0.5 and 1.0 mM). Absorbance of the supernatant was measured at 280 nm after 7 days incubation in 10 mM PBS buffer at pH 7.4. The absorbance was measured after centrifugation at 24° C. for 20 min. The relative centrifugal force used was $1.75 \times 10^4$ g. The measured absorbance is directly proportional to the concentration of polypeptide remaining in solution after incubation.

FIGS. 5A-5D. Biological Activity of wild-type hIAPP and exemplary mutant-hIAPP polypeptides. Concentration-response curves of cAMP production by wild-type hIAPP (SEQ ID NO: 1) compared with (A, B) exemplary mutant-hIAPP polypeptide, mutant analog 1 (SEQ ID NO: 10) and another (C, D) mutant-hIAPP polypeptide, mutant analog 4 (SEQ ID NO: 22) at the human amylin receptor ($hAMY_{1-(a)}$; A, C) and human calcitonin receptor ($hCT_{(a)}$; B, D). Wild-type and mutant hIAPP were provided to Cos-7 cells expressing $hAMY_{1(a)}$ and $hCT_{(a)}$ receptors, and the impact of each polypeptide's activity on amylin responsive receptors was analyzed. Curves are plotted as a percentage of maximal hIAPP stimulated cAMP production and data points represent the mean±SEM from independent experiments. As shown, in both exemplary mutant-hIAPP analogs do not significantly alter amylin or calcitonin receptor activity when compared to wild-type hIAPP protein. As such, the mutant-hIAPP polypeptides of the present disclosure do not alter the biological activity of wild-type hIAPP.

Figure 6:
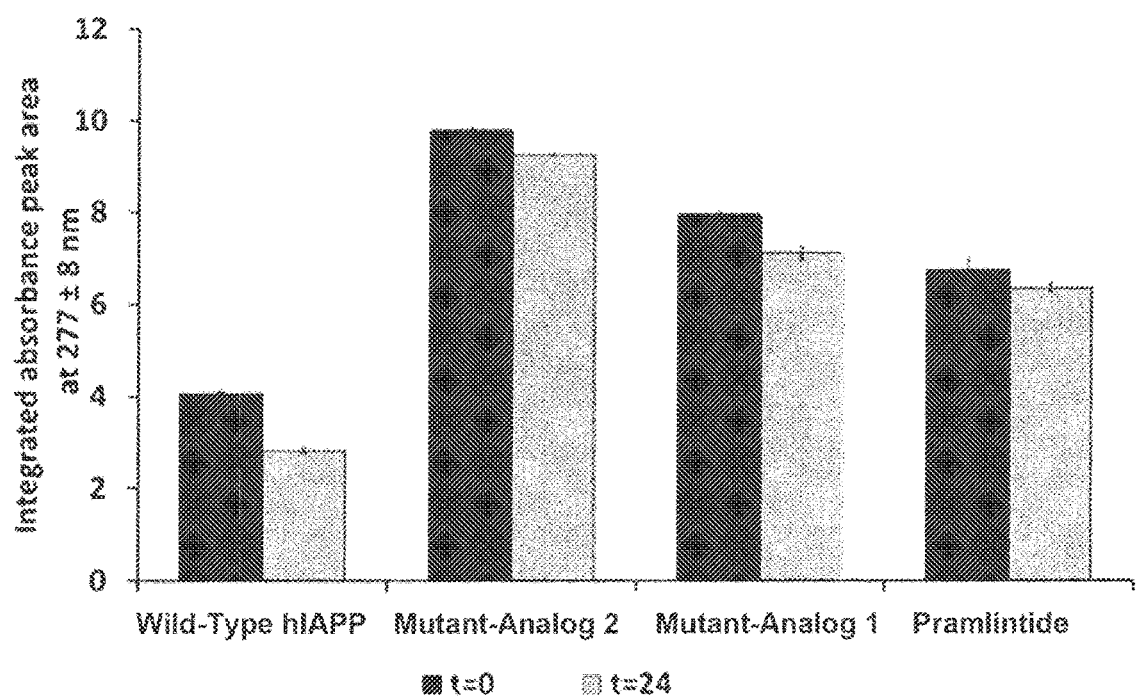

FIG. 6. Co-formulation of exemplary mutant-hIAPP polypeptides with human insulin. The solubility of wild-type hIAPP (SEQ ID NO: 1) and an existing FDA approved hIAPP polypeptide (paramlintide; SEQ ID NO: 2) co-formulated with purified human insulin at neutral pH was compared to the solubility of exemplary mutant-hIAPP polypeptides co-formulated with insulin. The solubility of the peptides was measured by absorbance measurement at 277 nm using liquid chromatography-mass spectroscopy (LC-MS). Exemplary mutant-hIAPP polypeptides (mutant analog 1, SEQ ID NO: 10; and mutant analog 2; SEQ ID NO: 16) exhibited a significantly higher absorbance when compared to both wild-type hIAPP and paramlintide when co-formulated at neutral pH. Taken together, the data shows that that the mutant-hIAPP polypeptides of the present disclosure are not only soluble when co-formulated with natural insulin at neutral pH, but are more soluble than wild-type hIAPP and other known therapeutic molecules when co-formulated with insulin at neutral pH. Error bars are the apparent standard deviation of 2 measurements.

Figures 7A, 7B:
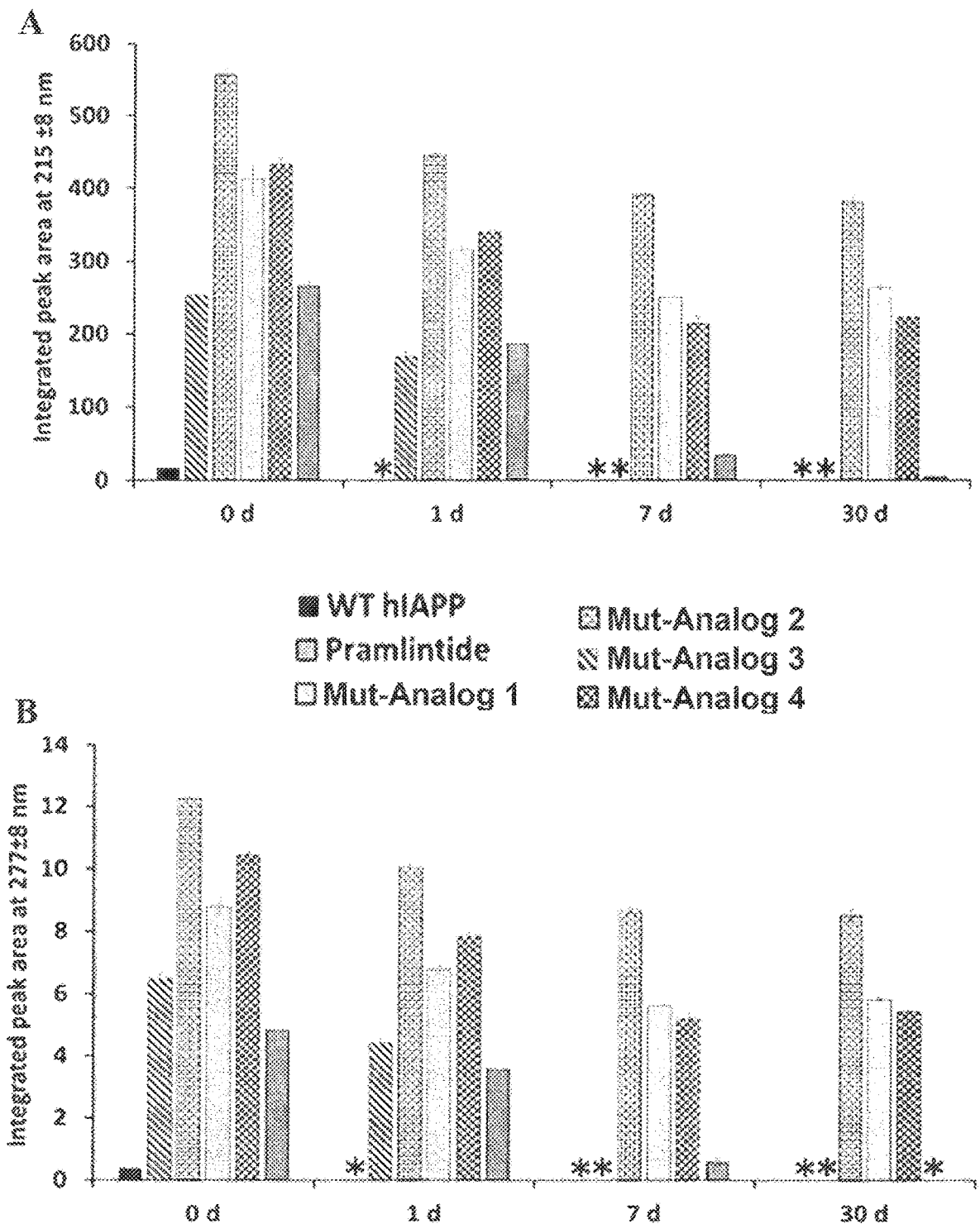

FIGS. 7A-7B. Co-formulation of exemplary mutant-hIAPP polypeptides with a synthetic insulin. The solubility of wild-type hIAPP (SEQ ID NO: 1) and an existing FDA-approved hIAPP polypeptide (paramlintide; SEQ ID NO: 2) co-formulated with a known FDA-approved synthetic insulin (Novolin-N®) at neutral pH was compared to the solubility of exemplary mutant-hIAPP polypeptides co-formulated with Novolin-N®. Samples were collected after formulation with Novolin-N® solution at time t=0, centrifuged and the supernatant of the co-formulation was freeze dried. Samples were collected again following the same procedure after 1 day, 7 days and 30 days. The solubility of the peptides was measured by absorbance measurement at 215 nm (A) and 277 nm (B) using LC-MS. Exemplary mutant-hIAPP polypeptides (mutant analog 1, SEQ ID NO: 10; and mutant analog 2; SEQ ID NO: 8; mutant analog 3; SEQ ID NO: 7; and mutant analog 4, SEQ ID NO: 22) exhibited a significantly higher absorbance when compared to both wild-type hIAPP and paramlintide when co-formulated at neutral pH. Taken together, the data shows that the mutant-hIAPP polypeptides of the present disclosure are not only soluble when co-formulated with natural insulin at neutral pH, but are also soluble when co-formulated with known synthetic insulin compositions. Furthermore, the mutant-hIAPP polypeptides of the present disclosure are more soluble than wild-type hIAPP and other known therapeutic hIAPP peptides when co-formulated with synthetic insulin at neutral pH. "*" indicates no measurable absorbance detected. Error bars are the apparent standard deviation of 2 measurements.

Table 1. Endogenous amylin receptor activity for mutant-hIAPP polypeptides compared to wild-type hIAPP. Each of the exemplary mutant-hIAPP polypeptides tested (i.e., mutant analog 1, SEQ ID NO: 10; and mutant analog 2; SEQ ID NO: 8; mutant analog 3, SEQ ID NO: 7; and mutant analog 4, SEQ ID NO: 22) retain the ability to bind the human calcitonin receptor ($hCT_{(a)}$) and the human amylin receptor ($hAMY_{1(a)}$), when compared to wild-type hIAPP (SEQ ID NO: 1). As such, each of the exemplary mutant-hIAPP polypeptides tested are biologically activity. $pEC_{50}$ equals, $-\log 10(EC_{50})$.

DETAILED DESCRIPTION OF THE DISCLOSURE

In general, the terms used herein comport with their usage by persons of skill in the field of the present disclosure. To facilitate an understanding of the embodiments of the disclosure as herein described, a number of terms, set off in quotation marks in this specification, are further explained herein. As used in this specification and its appended claims, terms such as "a", "an" and "the" are not intended to refer to only a singular entity, but include the general class of which a specific example may be used for illustration, unless the context dictates otherwise. The terminology herein is used to describe specific embodiments of the invention, not to limit the scope of the disclosure.

Human islet amyloid polypeptide (hIAPP) or amylin is coproduced with insulin in the islet β-cells of the pancreas and acts as a hormone involved in the regulation of adiposity and carbohydrate metabolism. As shown in FIG. 1, the mature, wild-type hIAPP polypeptide is 37 amino acid residues in length and has the amino acid sequence set forth in SEQ ID NO: 1. Notable post-translational modifications include a Cys-2 to Cys-7 disulfide bridge and an amidated C-terminus. hIAPP is the major protein component of amyloid plaques, which develop in pancreatic islets of type-2 diabetic patients. Moreover, the process of amyloid formation is toxic to insulin-producing β-cells, leading to islet cell stress, dysfunction and death, as well as islet transplant failure in subjects with diabetes.

Mutant-hIAPP Compositions

The present disclosure has elucidated that substitution of certain amino acids within the wild-type human hIAPP amino acid sequence results in improved polypeptide solubility at neutral pH when compared to wild-type hIAPP and other modified hIAPP polypeptides, such as FDA approved therapeutic peptide pramlintide (i.e., SYMLIN™), which has an amino acid sequence of KCNTATCATNRLAN-FLVHSSNNFGPILPPTNVGSNTY —(NH2) (SEQ ID NO: 2), in which the three amino acids at positions 25, 28 and 29 each are substituted to Proline when compared to the wild-type hIAPP polypeptide set forth in SEQ ID NO: 1.

Furthermore, the amino acid substitutions disclosed do not alter endogenous amylin function, and do not aggregate to form harmful amyloid plaques associated with amyloid based diseases.

Therefore, in a first aspect of the present disclosure, mutated analogs of wild-type hIAPP polypeptides (mutant-hIAPP polypeptides) are provided. The mutant-hIAPP polypeptides of the present disclosure are at least 37 amino acids in length and modify the structure (i.e., amino acid sequence) of the wild-type hIAPP protein and have unique properties when compared to the wild-type hIAPP protein. As such, the mutant-hIAPP polypeptides of the present disclosure do not occur in nature.

The term "peptide", "polypeptide" or "protein" are used interchangeably and refer to a linear series of amino acid residues linked to one another by peptide bonds between the alpha-amino and carboxy groups of adjacent amino acid residues.

The term "wild-type hIAPP", "amylin" or "human islet amyloid polypeptide (hIAPP)", are used interchangeably herein to mean a polypeptide including the first 37 amino acids of the human peptide hormone of Accession no. AAA35524. For example, wild-type hIAPP polypeptides of the present disclosure include the amino acid sequence KCNTATCATQRLANFLVHSSNNFGAILSSTNVGSNTY —(NH2) (SEQ ID NO: 1). Where —(NH2) indicates an amidated c-terminal amino acid. The term "amylin" or "hIAPP" also includes homologs of amylin as present in, and in isolatable form, other mammalian species.

By "homologs" it is meant that the corresponding amylin proteins of other vertebrate species are substantially homologous at the overall protein (i.e., mature protein) level to hIAPP. In certain embodiments, homologs of a hIAPP polypeptides have an amino acid sequence substantially identical to the human wild-type hIAPP polypeptide, i.e., at least 80-85%, at least 90-95% or more sequence identity. Further, homologs of hIAPP proteins retain the same physiological effects as wild-type amylin, including, for example, glucose regulation. Certain examples of homologs of the human amylin protein include, mouse, and rat amylin.

The term "mutant-hIAPP polypeptide", "mutant-hIAPP analog" "mutant-analog" and "mutant-hIAPP peptide" are used interchangeably herein to mean an amylin analog peptide having a substantially identical amino acid sequence to a peptide provided herein and in which one or more amino acid residues have been conservatively or non-conservatively substituted. The substitution of a polar residue such as Lysine, Arginine, Glutamine, Ornithine or Asparagine for another polar residue. Examples of non-conservative substitutions include the substitution of a non-polar residue, e.g., Isoleucine, Valine, Alanine or Methionine for a polar residue e.g., Asparagine, Glutamine, Glutamate, Ornithine, Lysine, and/or a polar residue for a non-polar residue. A mutant-hIAPP analog can have at least 75%, at least 80%, at least 85%, at least 90%, at least 91%, at least 92% sequence identity to SEQ ID NO: 1. For example, mutant-hIAPP analogs of the present disclosure include peptides having at least 75%, 76%, 77%, 78%, 79%, 80%, 81%, 82%, 83%, 84%, 85%, 86%, 87%, 88%, 89%, 90%, 91%, 92%, 93%, 94% or 95% sequence identity to SEQ ID NO: 1.

The term "amino acid" or "amino acid residue" as used herein shall mean natural amino acids, unnatural amino acids, and modified amino acid. Unless stated to the contrary, any reference to an amino acid, generally or specifically by name, includes reference to both the D and the L stereoisomers if their structure allow such stereoisomeric forms. For example, natural amino acids include, Ornithine, Alanine (Ala, A), Arginine (Arg, R), Asparagine (Asn, N), Aspartic acid (Asp, D), Cysteine (Cys, C), Glutamine (Gin, Q), Glutamic acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y) and Valine (Val, V).

In one embodiment of the present disclosure, mutant-hIAPP polypeptides have at least one amino acid substitution relative to the amino acid sequence of the wild-type hIAPP protein. In one instance, mutant-hIAPP polypeptides are provided that, when compared to the wild-type hIAPP amino acid sequence of SEQ ID NO: 1, include an amino acid substitution in at least one of the following positions of the wild-type hIAPP amino acid sequence: 21, 22, 31 and 35. Here, the mutant-hIAPP polypeptide can differ from the wild-type hIAPP amino acid sequence by only one amino acid or more than one amino acid. One exemplary mutant-hIAPP polypeptide includes an amino acid substitution at position 21, relative to the wild-type hIAPP amino acid sequence. Another mutant-hIAPP polypeptide includes an amino acid substitution at position 22, relative to the wild-type hIAPP amino acid sequence. Yet another exemplary mutant hIAPP polypeptide includes an amino acid substitution at position 31, relative to the wild-type hIAPP amino acid sequence. In another embodiment, the mutant hIAPP polypeptide of the present disclosure includes an amino acid substitution at position 35, relative to the wild-type hIAPP amino acid sequence.

In certain embodiments, the mutant-hIAPP polypeptides of the present disclosure contain an amino acid substitution from Asparagine to Lysine and/or Asparagine to Arginine at one or more of the following positions: 21, 22, 31 and 35. In some embodiments, the mutant-hIAPP polypeptide of the present disclosure has an amino acid substitution from Asparagine to Lysine and/or Asparagine to Arginine at two or three of the following positions: 21, 22, 31 and 35. In another embodiment, the mutant-hIAPP polypeptide has an amino acid substitution from Asparagine to Lysine or Asparagine to Arginine at all four of the following positions: 21, 22, 31 and 35. In other embodiments, Asparagine at any of the foregoing amino acid positions is replaced by Ornithine. In certain instances, the mutant hIAPP polypeptide has one or more of the following amino acid substitutions: N21K, N22K, N31K, N35K, N21R, N22R, N31R, N35R and any combination thereof.

In some embodiments, the mutant-hIAPP polypeptide differs from the wild-type hIAPP amino acid sequence by only one amino acid at one of the following amino positions, 21, 22, 31 and 35. For example, the mutant-hIAPP polypeptide can contain an amino acid substitution at position 21, relative to the wild-type hIAPP amino acid sequence, whereby the remaining amino acid residues correspond to that of the wild-type hIAPP polypeptide of SEQ ID NO: 1. In another example, the mutant-hIAPP polypeptide contains an amino acid substitution at position 22, relative to the wild-type hIAPP amino acid sequence, whereby the remaining amino acid residues correspond to that of the wild-type hIAPP polypeptide of SEQ ID NO: 1. Another exemplary mutant-hIAPP polypeptide has an amino acid substitution at position 31, relative to the wild-type hIAPP amino acid whereby the remaining amino acid residues correspond to that of the wild-type hIAPP polypeptide of SEQ ID NO:1. Yet another example provides a mutant-hIAPP polypeptide of the present disclosure that contains an amino acid substitution at position 35, relative to the wild-type hIAPP amino acid sequence, whereby the remaining amino acid residues correspond to that of the wild-type hIAPP polypeptide.

In other embodiments, when compared to the wild-type hIAPP amino acid sequence, the mutant-hIAPP polypeptides of the instant disclosure include an amino acid substitution in at least two of the following positions: 21, 22, 31 and 35. In yet other embodiments, the mutant-hIAPP polypeptides of the instant disclosure include an amino acid substitution in at least three of the following positions: 21, 22, 31 and 35, when compared to the wild-type hIAPP amino acid sequence. In another instance, the mutant-hIAPP polypeptide of the instant disclosure includes an amino acid substitution at each of the following positions: 21, 22, 31 and 35, when compared to the wild-type hIAPP amino acid sequence.

In a specific embodiment of the present disclosure, the mutant-hIAPP polypeptide includes at least two of the following amino acid substitutions: N21K, N21R, N35K, or N35K, such as in the exemplary mutant-hIAPP polypeptides set forth in SEQ ID NO: 3, SEQ ID NO: 4, SEQ ID NO: 7, SEQ ID NO: 8, SEQ ID NO: 11, SEQ ID NO: 12, SEQ ID NO: 15, SEQ ID NO: 17, SEQ ID NO: 18 and SEQ ID NO: 19. In specific embodiments of the present disclosure, the mutant-hIAPP polypeptide contains only the following amino acid substitutions: N21K and N35K as set forth in SEQ ID NOs: 3 and 7.

In another embodiment of the present disclosure, the mutant-hIAPP polypeptide includes at least two of the following amino acid substitutions relative to the wild-type hIAPP amino acid sequence: N22K, N22R, N31K or N31R, such as those polypeptides set forth in SEQ ID NO: 5, SEQ ID NO: 6, SEQ ID NO: 9, SEQ ID NO: 10, SEQ ID NO: 13, SEQ ID NO: 14, SEQ ID NO: 16, SEQ ID NO: 20, SEQ ID NO: 21, and SEQ ID NO: 22. In specific embodiments of the present disclosure, the mutant-hIAPP polypeptide contains only the following amino acid substitutions: N22K and N31K as set forth in SEQ ID NOs: 5 and 9.

In certain instances, the mutant-hIAPP polypeptides of the present disclosure include an amino acid substitution at at least one of the following amino acid positions: 21, 22, 31 and 35 as well as at least one Proline residue substitution relative to the wild-type hIAPP amino acid sequence set forth in SEQ ID NO: 1.

Therefore, some embodiments of the present disclosure provide mutant-hIAPP polypeptides that include an amino acid substitution at any one of the following positions: 21, 22, 31 and 35, or a combination thereof and a single Proline residue substitution at one of the following positions: 24, 25, 26, 28 and 29 (e.g., G24P, A25P, I26P, S28P, S29P), relative to the wild-type hIAPP amino acid sequence. In yet another embodiment, the mutant-hIAPP polypeptides of the present disclosure can include an amino acid substitution at any two or three of the following positions: 21, 22, 31 and 35 and a single Proline residue substitution at one of the following positions: 24, 25, 26, 28 or 29. In another embodiment, the mutant-hIAPP polypeptides of the present disclosure include an amino acid substitution at all four of the following positions: 21, 22, 31 and 35 and a Proline residue substitution in at least two of the following positions: 24, 25, 26, 28 or 29.

In specific embodiments, the mutant-hIAPP polypeptides of the present disclosure include an Asparagine to Lysine or Arginine substitution at positions 21, 22, 31, 35 or combinations thereof. In a non-limiting example, mutant-hIAPP polypeptides of the present disclosure include an Asparagine to Lysine or Asparagine to Arginine substitution at positions 21 and 31 and a single Proline residue substitution at one of positions 24, 26 or 28. In another example, mutant-hIAPP polypeptides of the present disclosure include an Asparagine to Lysine or Asparagine to Arginine substitution at positions 22 and 35 and a single Proline residue substitution at one of positions 24, 26 or 28. In yet another non-limiting example, mutant-hIAPP polypeptides of the present disclosure include an Asparagine to Lysine or Asparagine to Arginine substitution at positions 21 and 22 and a single Proline residue substitution at one of positions 24, 26 or 28. In yet another non-limiting example, mutant-hIAPP polypeptides of the present disclosure includes an Asparagine to Lysine or Asparagine to Arginine substitution at positions 31 and 35, and a single Proline residue substitution at one of positions 24, 26 or 28.

In an exemplary embodiment, the mutant-hIAPP polypeptides of the present disclosure can include an amino acid substitution at any two of the following positions: 21, 22, 31 and 35 and a single Proline residue substitution at one of the following positions: 24, 25, 26, 28 or 29. In specific embodiments of the present disclosure, the mutant-hIAPP polypeptide includes two of the following amino acid substitutions relative to the wild-type hIAPP amino acid sequence: N21K, N22K, N31K, N35K, N21R, N22R, N31R, N35R, and a single Proline residue substitution at one of the following positions: 24, 25, 26, 28 or 29, such as those polypeptides set forth in SEQ ID NO: 11, SEQ ID NO: 17, SEQ ID NO: 12, SEQ ID NO: 18, SEQ ID NO: 15, SEQ ID NO: 19, SEQ ID NO: 13, SEQ ID NO: 20, SEQ ID NO: 14, SEQ ID NO: 21, SEQ ID NO: 16, and SEQ ID NO: 22.

More specifically, a mutant-hIAPP polypeptide can have an amino acid sequence set forth in any one of the following amino acid sequences: SEQ ID NO: 11, SEQ ID NO: 12 SEQ ID NO: 13, SEQ ID NO: 14, SEQ ID NO: 15 and SEQ ID NO: 16.

In other embodiments, the mutant-hIAPP polypeptides of the present disclosure set forth in SEQ ID NO: 11, SEQ ID NO: 12, SEQ ID NO: 13, SEQ ID NO: 14, SEQ ID NO: 15 and SEQ ID NO: 16 has an amidated c-terminal such as one of the exemplary mutant-hIAPP polypeptides: SEQ ID NO: 17, SEQ ID NO: 18, SEQ ID NO: 19, SEQ ID NO: 20, SEQ ID NO: 21, and SEQ ID NO: 22.

In certain embodiments, the mutant-hIAPP polypeptide includes an amino acid substitution at any two of the following positions: 21, 22, 31 and 35 and a Proline residue substitution in at least two of the following positions: 24, 25, 26, 28 or 29. Here, the mutant-hIAPP polypeptides of the present disclosure can include an Asparagine to Lysine or Asparagine to Arginine substitution at two of the following positions 21, 22, 31, 35 and a Proline substitution at two or more of the following positions: 24, 25, 26, 28 or 29, relative to the wild-type hIAPP protein. In another embodiment, the mutant-hIAPP polypeptide of the present disclosure includes an amino acid substitution at any two of the following positions: 21, 22, 31 and 35 and at least two Proline residue substitutions at two of the following positions: 24, 25, 26, 28 or 29.

In an exemplary embodiment, mutant-hIAPP polypeptides of the present disclosure include an Asparagine to Lysine or Asparagine to Arginine substitution at two of the following positions 21, 22, 31, 35 and a Proline residue substitution at two of the following positions in the wild-type hIAPP protein sequence: 24, 26 or 28. In a non-limiting example, mutant-hIAPP polypeptides of the present disclosure include an Asparagine to Lysine or Arginine substitution at positions 21 and 31 and a Proline residue substitution at any two of amino acids 24, 26 or 28 of the wild-type hIAPP protein sequence. In another example, mutant-hIAPP polypeptides of the present disclosure include an Asparagine to Lysine or Asparagine to Arginine substitution at positions 22 and 35 and a Proline residue substitution at any two of amino acids 24, 26 or 28 of the wild-type hIAPP protein sequence. In yet another example, mutant-hIAPP polypeptides of the present disclosure include an Asparagine to Lysine or Asparagine to Arginine substitution at positions 21 and 22 and a Proline residue substitution at any two of amino acids 24, 26 or 28 of the wild-type hIAPP protein sequence. In yet another non-limiting example, mutant-hIAPP polypeptides of the present disclosure includes an Asparagine to Lysine or Asparagine to Arginine substitution at positions 31 and 35, and a Proline residue substitution at any two of amino acids 24, 26 or 28 of the wild-type hIAPP protein sequence.

In specific embodiments, the mutant-hIAPP polypeptide contains only the following amino acid substitutions relative to the wild-type hIAPP amino acid sequence: N21K, G24P, I26P, N35K as set forth in SEQ ID NO: 4 and SEQ ID NO: 8. In another specific embodiment, the mutant-hIAPP polypeptide contains only the following amino acid substitutions N22K, G24P, I26P, N31K as set forth in SEQ ID NOs: 6 and SEQ ID NO:10.

In particular instances, the mutant-hIAPP polypeptide of the present disclosure has the following amino acid sequence:

```
                                           (SEQ ID NO: 3)
KCNTATCATQRLANFLVHSSKNFGAILSSTNVGSKTY, (SEQ ID NO: 4)
KCNTATCATQRLANFLVHSSKNFPAPLSSTNVGSKTY, (SEQ ID NO: 5)
KCNTATCATQRLANFLVHSSNKFGAILSSTKVGSNTY, (SEQ ID NO: 6)
KCNTATCATQRLANFLVHSSNKFPAPLSSTKVGSNTY, (SEQ ID NO: 11)
KCNTATCATQRLANFLVHSSKNFPAILSSTNVGSKTY, (SEQ ID NO: 12)
KCNTATCATQRLANFLVHSSKNFGAPLSSTNVGSKTY, (SEQ ID NO: 13)
KCNTATCATQRLANFLVHSSNKFPAILSSTKVGSNTY, (SEQ ID NO: 14)
KCNTATCATQRLANFLVHSSNKFGAPLSSTKVGSNTY, (SEQ ID NO: 15)
KCNTATCATQRLANFLVHSSKNFGAILPSTNVGSKTY,
and (SEQ ID NO: 16)
KCNTATCATQRLANFLVHSSNKFGAILPSTKVGSNTY.
```

Even further, in some instances the mutant-hIAPP polypeptides of the present disclosure have an amidated c-terminus (i.e., Y—NH$_2$). As such in particular instances the mutant-hIAPP polypeptide of the present disclosure having an amidated c-terminus has the following amino acid sequence:

```
                                           (SEQ ID NO: 7)
KCNTATCATQRLANFLVHSSKNFGAILSSTNVGSKTY-NH2, (SEQ ID NO: 8)
KCNTATCATQRLANFLVHSSKNFPAPLSSTNVGSKTY-NH2, (SEQ ID NO: 9)
KCNTATCATQRLANFLVHSSNKFGAILSSTKVGSNTY-NH2, (SEQ ID NO: 10)
KCNTATCATQRLANFLVHSSNKFPAPLSSTKVGSNTY-NH2, (SEQ ID NO: 17)
KCNTATCATQRLANFLVHSSKNFPAILSSTNVGSKTY-NH2,
```

-continued

KCNTATCATQRLANFLVHSSKNFGAPLSSTNVGSKTY-NH$_2$, (SEQ ID NO: 18)

KCNTATCATQRLANFLVHSSKNFGAILPSTNVGSKTY-NH$_2$, (SEQ ID NO: 19)

KCNTATCATQRLANFLVHSSNKFPAILSSTKVGSNTY-NH$_2$, (SEQ ID NO: 20)

KCNTATCATQRLANFLVHSSNKFGAPLSSTKVGSNTY-NH$_2$, and (SEQ ID NO: 21)

KCNTATCATQRLANFLVHSSNKFGAILPSTKVGSNTY-NH$_2$. (SEQ ID NO: 22)

The mutant-hIAPP polypeptides of the present disclosure, homologs, and analogs thereof can be synthetic proteins, synthesized by a number of known techniques. The term "synthetic peptide" or "synthetic polypeptide" as used herein refers to a chemically derived chain of amino acid residues linked together by peptide bonds that are isolated or substantially isolated from other materials or elements. Certain non-limiting examples of synthetic peptide production methods include, solid-phase peptide synthesis, Solid-Phase Peptide Synthesis by FMOC (Fluorenylmethyloxycarbonyl) Chemistry and Solid-Phase Peptide Synthesis by t-BOC (tert-butyloxycarbonyl) Chemistry (also referred to as BOC chemistry).

For example, the peptides of the present disclosure can be prepared using the solid-phase synthetic technique initially described by Merrifield, in *J. Am. Chew. Soc.* 85, pp. 2149-2154 (1963). Other peptide synthesis techniques can be found in M. Bodanszky, et al., *Peptide Synthesis*, John Wiley & Sons, 2d Ed., (1976) and other references readily available to those skilled in the art. A summary of polypeptide synthesis techniques can be found in J. Stuart and J. D. Young, Solid Phase Peptide Synthesis, Pierce Chemical Company, Rockford, Ill., (1984). Peptides can also be synthesized by solution methods as described in The Proteins, Vol. II. 3d Ed., Neurath, H. et al., Eds., p. 105-237, Academic Press. New York, N.Y. (1976). Appropriate protective groups for use in different peptide syntheses are described in the above-mentioned texts as well as in J. F. W. McOmie, *Protective Groups in Organic Chemistry*, Plenum Press, New York, N.Y. (1973). The polypeptides of the present disclosure can also be prepared by chemical or enzymatic cleavage from larger portions of the amylin protein or from the entire endogenous amylin protein.

Specific examples of conventional techniques include methods such as solid-phase technique. In general, the solid-phase method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as Lysine, Asparagine, Cysteine, Glutamine, Aspartic acid, Glutamic acid, Threonine, Serine, Tyrosine and Arginine, A preferred method of solid phase synthesis the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino carboxyl group is then removed from this newly added amino acid residue, and the next amino acid (suitably protected) is then added, and so forth. After all the desired amino acids have been linked in the proper sequence, any remaining terminal and side group protecting groups including the solid support are removed sequentially or concurrently to yield the final peptide. The peptide is treated to form the disulfide bond between residues 2 and 7, for example, by incubation in solutions containing dimethyl sulfoxide (DMSO) at room temperature and then purified to yield the final peptide. See, for example, Abedini, A., et al *Anal. Biochem.* (2006) Vol. 351, pp. 181-186.

The mutant-hIAPP peptides of the present disclosure can also be recombinantly-produced peptides. The term "recombinantly-produced" or "recombinant protein" as used herein generally refers to transfecting or transducing cells with a nucleic acid vector that contains the a nucleotide sequence that encodes for a protein (i.e., mutant-hIAPP polypeptide), culturing the cells so that the nucleic acid is expressed and subsequently translated into the desired protein. Cells can then be lysed to extract the expressed protein of interest for subsequent isolation and purification. Both prokaryotic and eukaryotic in vivo protein expression systems are widely used and will be known by those of ordinary skill in the art. In certain embodiments recombinantly-produced proteins may be developed using cell-free or in vitro synthesis methods. Such cell-free methods generally include whole cell extracts containing all the macromolecule components needed for transcription, translation and post-translational modification. These components include RNA polymerase, regulatory protein factors, transcription factors, ribosomes, and tRNA, which when supplemented with cofactors, nucleotides and the specific nucleic acid template containing a coding sequence (DNA or mRNA transcript) that corresponds to a mutant-hIAPP polypeptide.

Such recombinant DNA techniques are known by one of ordinary skill in the art. See, e.g., Current Protocols in Molecular Cloning Ausubel et al., ed. (1995), John Wiley & Sons, New York); Sambrook et al., (1989), Molecular Cloning: A Laboratory Manual, Second Edition, Cold Spring Harbor Laboratory Press, New York; Coligan et al. *Current Protocols in Immunology*, John Wiley &. Sons Inc., New York, N.Y. (1994); see, also, Williamson J. A. and Miranker, A. D., Protein Science (2007) Vol. 16, pp. 110-117, and Camargo, D C R et al *Protein Expression and Purification* (2015) Vol. 106, pp. 49-56 (describing the use of an intenin based expression systems that enable the development of amidated c-terminal proteins).

The skilled artisan understands that any of a wide variety of expression systems can be used to obtain the recombinant peptides of the present invention. The precise host cell used is not critical to the present methods. The peptides of the present disclosure can be produced in a prokaryotic host (e.g., *E. coli* intenin-based systems), or in a eukaryotic host (e.g., *S. cerevisiae* or mammalian cells, such as COS1, CHO, NIH3T3, and JEG3 cells, or in the cells of an arthropod, for example, *S. frugiperda*). Such cells are available from, for example, the American Type Culture Collection, Manassas, Va. It is appreciated by the skilled artisan that the method of transfection and the choice of expression vehicle will depend on the host system selected. Transformation and transfection methods are described, e.g. in Sambrook et al., (1989); expression vehicles can be chosen from those provided. See, e.g., P. H. Powels et al., Cloning Vectors: A Laboratory Manual. (1985).

For most of the amino acids used to build proteins, more than one coding nucleotide triplet (codon) can code for a particular amino acid residue. This property of the genetic code is known as redundancy. Therefore, a number of different nucleotide sequences can code for a particular peptide corresponding to the mutant-hIAPP polypeptides of the present disclosure. The present disclosure also contemplates a deoxyribonucleic acid (DNA) molecule or segment that defines a gene coding for, i.e., capable of expressing, a subject peptide or a subject chimeric peptide from which a peptide of the present disclosure can be enzymatically or chemically cleaved.

Nucleic acid molecules such as deoxy-ribonucleic acid (DNA) and ribonucleic acid (RNA) molecules that encode the polypeptides of the present disclosure can be synthesized by chemical techniques, for example, the phosphotriester method of Matteuccie, et al., *J. Am. Chem. Soc.* (1981) Vol. 103, pp. 3185, which is incorporated herein by reference. Using a chemical DNA synthesis technique, desired modifications in the peptide sequence can be made by making substitutions for nucleotide bases, which code for the native amino acid sequence. Ribonucleic acid equivalents of the above described DNA molecules can also be used. Therefore, a nucleic acid molecule comprising a vector capable of replication and expression of a nucleic acid molecule (RNA, DNA) coding sequence for a mutant-hIAPP polypeptide is also contemplated.

In an exemplary embodiment of the present disclosure, the mutant-hIAPP polypeptides are synthetic peptides. Synthetic mutant-hIAPP polypeptides can be created using Solid-Phase Peptide Synthesis by 9-fluornylmethoxycarbonyl (Fmoc) Chemistry. For example, a mutant-hIAPP polypeptide is synthesized on a 0.1 mmol scale using a microwave peptide synthesizer using Fmoc chemistry carried out under standard Fmoc reaction cycles. Whereby the use of a 5-(4'-Fmoc-aminomethyl-3',5-dimethoxyphenol) valeric acid (PAL-PEG) resin affords the ability to amidate the C-terminus of any exemplary peptide. Amino acids can be dissolved in 1-methyl-2-pyrrolidone and deprotection of Fmoc group is achieved using a mixture of 20% (v/v) piperidine in N,N-dimethylformamide. The deprotection can be conducted at 40 watts microwave power, with the temperature starting at 30° C. and gradually increasing to 77° C. within the total microwave time of 3 minutes. Amino acid coupling reactions are then carried out using 0.45 M 2-(1H-benzotriazole-1-yl)-1,1,3,3-tetramethyluronium hexafluorophosphate in N,N-dimethylformamide as an activator and 2 M N,N-Diisopropylethylamine in 1-methyl-2-pyrrolidone as an activator base. The coupling reactions are conducted at 35 watts microwave power, with the temperature starting at 35° C. and gradually increasing to 80° C. within the total microwave time of 5 minutes. This method can be used applied to all amino acid residues except Cys, His and Arg. Cys and His can be coupled with no microwave power, with the starting temperature of 15° C. and gradually increasing to 48° C. within a total reaction time of 15 minutes. Arg is coupled with no microwave power, with the starting temperature of 15° C. and gradually increasing to 75° C. within a total reaction time of 30 min. The first residue can attach to a resin, pseudoproline dipeptide derivatives and all β-branched residues can be double coupled. Fmoc-Ala-Thr ($\Psi^{Me,Me}$pro)-OH at position 8-9, Fmoc-Ser (tBu)-Ser ($\Psi^{Me,Me}$pro) at position 19-20, and Fmoc-Leu-Ser ($\Psi^{Me,Me}$pro)-OH at position 27-28 can be utilized when applicable. Peptides can then be released from the resin using 90% trifluoroacetic acid, 3.33% anisole, 3.33% thioanisole and 3.33% ethanedithiol with shaking at room temperature. The reaction mixture can then be filtered over a funnel to reduce the liquid fraction until the sample reaches a desired volume (e.g., 0.4 ml). The resulting liquid is then treated with cold diethyl ether to precipitate the crude peptide. The peptide is then isolated using a fine fritted funnel. The peptide can then be dried by lyophilization and dissolved in 20% (v/v) acetic acid and lyophilized before oxidation and purification to improve the solubility of the peptides. The peptides can be oxidized in 100% dimethyl sulfoxide at room temperature with continuous shaking and then purified via reverse-phase high-performance liquid chromatography (RP-HPLC) using a buffered column gradient.

In certain embodiments, Fmoc chemistry includes the incorporation of two or three oxazolidine pseudoproline dipeptide derivatives, with double coupling of alpha-branched residues, pseudoproline dipeptide derivatives, and residues according to the protocol described in Marek, P., et al. *Org. Lett.* (2010) Vol. 12, pp. 4848-4851 and Abedini A., and Raleigh D. *Org. Lett.* (2005) Vol. 7, pp. 693-696 the entire contents of both of which are incorporated herein by reference.

In another non-limiting embodiment of the present disclosure, the mutant-hIAPP are created using Solid-Phase Peptide Synthesis by T-Boc chemistry. The synthesis of proteins using T-Boc chemistry is well known by those of ordinary skill in the art and certain non-limiting examples of T-Boc Solid-Phase Peptide Synthesis can be found in Schnolzer M., et al., *International Journal of Peptide and Protein Research.* (1992) Vol. 40:3-4, pp. 180-193, the contents of which are incorporated herein by reference.

In certain preferred embodiments, the mutant-hIAPP polypeptide compositions of the present disclosure can be isolated and purified from various different sources to a level useful in a therapeutic application. The term "isolated" and "purified", when used in reference to a molecule (such as a peptide, protein or polypeptide), means that the molecule has been removed from its naturally occurring environment and is substantially free of other molecules (such as other proteins). By "substantially free" of other proteins, it is meant that a protein of interest accounts for at least 60%, 70%, 80%, 90%, or 95% (by dry weight) of total proteins in a composition. When an isolated protein is recombinantly produced, it can also be substantially free of culture medium, i.e., culture medium represents less than about 20% of the volume of the preparation, less than about 10% of the volume of the preparation or less than about 5% of the volume of the preparation. For example, the mutant-hIAPP polypeptides of the present disclosure can be purified to homogeneity or other varying degrees of purity. The level of purification can be based on the intended use. In certain non-limiting examples, the isolated mutant-hIAPP polypeptides of the present disclosure can be purified from cells that express such protein, as further described below, or can be synthetically made using known protein synthesis methods.

In certain embodiments, mutant-hIAPP analogs of the present disclosure can be isolated by a one or more of the following methods of: 1) concentration using a centrifuge, 2) gel filtration chromatography, and 3) reverse phase chromatography, specifically HPLC. In, for example, larger scale purification of mutant-hIAPP compositions of the present disclosure, forms of chromatography other than HPLC, such as fast protein liquid chromatography (FPLC) are useful and appropriate. Other forms of chromatography are also useful when isolating and/or purifying mutant-hIAPPs of the present disclosure, such as ion exchange, molecular sieve, or hydrophobic interaction chromatography In certain exemplary methods, the mutant-hIAPP proteins of the present disclosure are isolated and purified to further increase solubility, by partially dissolving crude peptides in 20% acetic acid (v/v), frozen in liquid nitrogen and lyophilized. This procedure can be repeated several times prior to purification. The dry peptides can then be redissolved in 35% acetic acid (v/v) and purified via reversed-phase HPLC. A two-buffer system can be used, including HCl as an ion pairing agent. For example, buffer 1 can include $H_2O$ and HCl, while buffer 2 contains acetonitrile, $H_2O$ and HCl. Purity can then be measured by HPLC. Here, two solvent systems can be used. The first is the same buffer 1 and 2 used for initial peptide purification. The second buffer system utilizes TFA as the ion pairing agent. Such as, for example, buffer 1 consists of $H_2O$ and TFA and buffer 2 consists of acetonitrile, $H_2O$ and TFA.

In certain embodiments of the present disclosure, mutant-hIAPPs are oxidized and analyzed by mass spectrometry (e.g., MALDI-TOF) to determine the purity of the mutant-hIAPP polypeptides.

Pharmacological Formulations.

As stated above, the present disclosure unexpectedly reveals that the mutant-hIAPP polypeptides of the present disclosure have the ability to be formulated at neutral pH with or without insulin (e.g., existing therapeutic insulin formulations), while retaining the biological function such as the ability to bind human calcitonin and human amylin receptors. Therefore, pharmacological formulations comprising neutral solutions that include one or more of the mutant-hIAPP polypeptides of the present disclosure are provided.

As such, in another aspect of the present disclosure one or more of the mutant-hIAPP polypeptides are formulated as a pharmacological composition at neutral pH.

The term "neutral", "neutral pH" or "physiological pH" as used herein disclosure shall mean a solution having about the same amount of free hydrogen and hydroxide ions. The complete pH scale, which is well known in the art, ranges from a pH of about 0 (most acidic) to a pH of about 14 (most basic or alkaline). The pH of a solution may be adjusted by the addition of aqueous solutions of hydrochloric acid (e.g., 10%) to increase the acidity of a solution (i.e., lowering the pH) and/or sodium hydroxide (e.g., 10%) to increase the pH (i.e., making the solution more basic). At the normal physiological temperature for humans, i.e., 37° C., neutral pH ranges from 6.7-7.8. More specifically, neutral pH formulations as used herein range from 6.8-7.4, 7.0-7.8, 7.0-7.4 and 7.4 to 7.8. In certain specific embodiments the mutant-hIAPP polypeptides of the present disclosure are formulated at a neutral pH of 7.2-7.4, 7.4 to 7.8 or 7.4.

The neutral pharmacological formulation can include at least one type of mutant-hIAPP polypeptide of the present disclosure, at least two types mutant-hIAPP, at least three different types of mutant-hIAPP polypeptides of the present disclosure or more. In a specific embodiment, the neutral pharmacological formulation contains at least one type of mutant-hIAPP polypeptide. In another embodiment, the neutral pharmacological formulation is a solution that includes at least two different mutant-hIAPP polypeptides of the present disclosure. In yet another embodiment, the neutral pharmacological formulation is a solution that includes two different mutant-hIAPP polypeptides of the present disclosure. In one instance, the neutral pharmacological formulation is a solution that includes a plurality of (i.e., more than 3) different mutant-hIAPP polypeptides of the present disclosure.

Methods for forming pharmacological solutions that include peptides, such as amylin or analogs thereof are well known by those of ordinary skill in the art, as evidenced by Cooper, et al., *Proc. Natl. Acad. Sci.* USA, (1987) Vol. 84, pp. 8628-8623, U.S. Patent Application Publication Number 2008/02489999 to Steiner, the entire contents of both of which is hereby incorporated by reference.

In certain non-limiting embodiments, the pharmacological compositions of the present disclosure include one or more of the mutant-hIAPP polypeptides of the present disclosure in an aqueous solution and at least one additive. As used herein the term "additive" can be any agent other than a mutant-hIAPP polypeptide. The term "agent" as used herein refers to any kind of composition or combination of compositions. In one embodiment of the present disclosure the agent is a small molecule. In another embodiment of the disclosure, the agent is a biological molecule, including, but not limited to, a protein, a polypeptide, an antibody or a nucleic acid.

The term "therapeutic agent" may be any agent that confers a therapeutic effect on a subject. Non-limiting examples of certain therapeutic agents that can be used in conjunction with the compositions and methods disclosed herein, include insulin or an synthetic analog thereof.

As used herein, "insulin" refers to human or non-human, recombinant, purified or synthetic insulin or insulin analogs having similar function and structure, unless otherwise specified. As used herein, "Human insulin" is the human peptide hormone secreted by the pancreas, whether isolated from a natural source or made by genetically altered microorganisms. As used herein, "non-human insulin" from an animal source such as pig or cow. As used herein, an insulin analog is an altered insulin, different from the insulin secreted by the pancreas, but still available to the body for performing the same action as natural insulin. Through genetic engineering of the underlying DNA, the amino acid sequence of insulin can be changed to alter its ADME (absorption, distribution, metabolism, and excretion) characteristics. Examples include insulin lispro, insulin glargine, insulin aspart, insulin glulisine insulin detemir. The insulin can also be modified chemically, for example, by acetylation. As used herein, human insulin analogs are synthetic human insulin which is able to perform the same: action as human insulin, such as (e.g., Humalog®, Apidra®, NovoLog®, Humulin®, Novolin®, Novolin-N®, Levemir® or combinations thereof), which may be employed to delivered to a subject at physiological pH.

An additive can be a "chelator" or "chelating agent", which refers to a chemical compound that has the ability to form one or more bonds to metal ions, e.g., zinc ions. The bonds are typically ionic or coordination bonds. The chelator can be an inorganic or an organic compound. A chelate complex is a complex in which the metal ion is bound to two or more atoms of the chelating agent. For example, a chelating agent can include Ethylenediaminetetraacetic acid (EDTA).

An additive can also be a "solubilizing agent", which is a compound that increases the solubility of materials in a solvent or example, insulin or a mutant-hIAPP polypeptide, in an aqueous solution. Examples of solubilizing agents include surfactants (TWEEN®); solvent, such as ethanol; micelle forming compounds, such as oxyethylene monostearate; and pH-modifying agents An additive for incorporation in a pharmacological formulation of the present disclosure can also be a "dissolution agent"; an acid that, when added to pharmacological formulation with Ethylenediaminetetraacetic acid (EDTA), enhances the transport and absorption of insulin or a mutant-hIAPP polypeptide relative to Hydrochloric acid (HCL) and EDTA at the same pH. HCl is not a dissolution agent but may be a solubilizing agent. Citric acid is a dissolution agent. For example, some acids mask charges on insulin, enhancing uptake and transport. Those acids which are effective as dissolution agents include acetic acid, ascorbic acid, citric acid, glutamic, aspartic, succinic, fumaric, maleic, and adipic. HCl may be used for pH adjustment, in combination with any of the formulations, but is not a dissolution agent.

An additive for incorporation in a pharmacological formulation of the present disclosure can also be an "excipient", which means an inactive substance other than a chelator or dissolution agent, used as a carrier for the insulin or used to aid the process by which a product is manufactured. In such cases, the active substance is dissolved or mixed with an excipient.

In certain embodiments, formulations of the present disclosure include a mutant-hIAPP polypeptide, a chelator and a dissolution agent(s) and, one or more other excipients as required to make a formulation suitable for administration to a subject. The choice of dissolution agent and chelator, the concentration of both the dissolution agent and the chelator, and the pH that the formulation is adjusted without undue experimentation by one of ordinary skill in the art to optimize the final pharmaceutical formulation.

For example, the additives comprising a pharmacological formulation of the present disclosure can be selected to dissolve rapidly in aqueous medium. Preferably the mutant-hIAPP is absorbed and transported to the plasma quickly, resulting in a rapid onset of action following administration.

A chelator, such as EDTA, chelates the zinc in insulin, thereby removing the zinc from a formulation that includes insulin. To the extent that the chelator (such as EDTA) and/or dissolution agent (such as citric acid) hydrogen bond with the insulin, it is believed that it masks the charge on the insulin, facilitating its transmembrane transport and thereby increasing both the onset of action and bioavailability for insulin.

In certain embodiments, the mutant-hIAPP polypeptide can be solubilized in a solution that includes water, and a phosphate buffer such as phosphate buffered saline (PBS), whereby the solution is maintained at neutral pH. In some instances, mutant-hIAPP polypeptides may be formulated either alone, or in combination, in aqueous solutions including, but not limited to, bacteriostatic water or preservative-free sterile water, preservatives (e.g., metacresol, benzyl alcohol), tonicity modifiers (e.g., D-mannitol), and a pH modifier (e.g., HCl, acetic acid and/or sodium acetate). In other embodiments certain inactive additives such as, glutamic acid, glycine, polysorbate 20, and sucrose, can be added.

Protein based therapeutic agents are often formulated with "inert" additives such as polymers. Accordingly, pharmacological formulations comprising mutant-hIAPP polypeptides of the present disclosure can include at least pharmaceutically acceptable carrier. For example, a polymer selected from the group consisting of alginates, chitosan, collagen, fibrins, methoxy poly(ethylene glycol), polyanhydrides, poly(caprolactone), poly(ethylene oxide), poly(lactic acid), poly-lactide-co-glycolide (PLGA), poly(ortho esters), polyethylene vinyl-co-acetate (EVAc), polyethylene glycol (PEG), polyester-PEG triblock copolymers, polyphosphazenes, poly[(sebacic-co-(ricinoleic acid)], ricinoleic acid, silicone, and multiple component combinations of the above.

Additionally, mutant-hIAPP polypeptides of the present disclosure may be artificially post-translationally modified with inert, covalently linked polymers such as PEG to slow clearance and increase "bioavailability" prior to or during formulation. Therefore, encompassed herein are pharmaceutical formulations that include modified forms of the mutant-hIAPP polypeptides of the present disclosure, such as various post-translationally modified forms thereof (e.g., glycosylated forms). Modified variants of the mutant-hIAPP polypeptides of the present disclosure are also envisioned herein. Accordingly, any of the mutant-hIAPP polypeptides disclosed herein can also include a chemical modification selected from the group consisting of amidation, lipidation, glycosylation, pegylation, acetylation and combinations thereof. The modification may be generated in vivo in cells or in vitro by chemically modifying the protein.

In exemplary embodiments, pharmacological formulation including a mutant-hIAPP polypeptide is prepared by incubating the peptide(s) in solutions containing DMSO (see, for example, Abedini, A., et al *Anal. Biochem.* (2006) Vol. 351, pp. 181-186), dissolution of mutant-hIAPP polypeptides in guanidinium solutions, e.g., guanidinium hydrochloride, pH 7.5, buffered in 0.2M sodium monohydrogen phosphate/sodium dihydrogen phosphate, or dissolution in a trifluoroacetic acid/acetonitrile solution, e.g., 1.0% trifluoroacetic acid/67% acetonitrile; dissolution in a formic acid solution, e.g., 70% formic acid; and the application of ultrasound to dissolve the mutant-hIAPP polypeptides in the neutral aqueous solution.

In other embodiments, the pharmacological formulation of the present disclosure includes at least one mutant-hIAPP polypeptide and at least one other therapeutic agent. For example, in some embodiments, the pharmacological formulation includes at least one mutant-hIAPP polypeptide and at least one other therapeutic agent, such as insulin. In certain embodiments the pharmacological formulation includes isolated endogenous insulin or synthetic insulin. In a specific instance the synthetic insulin is Humalog®, Apidra®, NovoLog®, Humulin®, Novolin®, Novolin-N®, Levemir® or a combination thereof.

In some embodiments, the isolated mutant-hIAPP polypeptides of the present disclosure are formulated at a pH of from 6.7-7.8, 7.0-7.8, 7.4 to 7.8, and 7.0-7.4, inclusive. In certain specific embodiments, the mutant-hIAPP polypeptides of the present disclosure are formulated at a neutral pH of 7.2-7.4 or 7.4. In some instances, the neutral pharmacological formulation of the present disclosure has a pH of between 7.2 and 7.6 or between 7.3 and 7.5. In an exemplary embodiment, the neutral pharmacological formulation is a solution that includes at least one mutant-hIAPP polypeptide of the present disclosure and has a pH of 7.4.

Therapeutic Methods

Amyloid formation including plaques of fibrils formed by aggregation of hIAPP are toxic to pancreatic beta-cells and islets and leads to pancreatic beta-cell death. See Westermark, P., et al. *Physiol. Rev.* (2011) Vol. 91, pp. 795-826. Furthermore, since the inventors have shown that the mutant-hIAPP polypeptides prevent amlyoid formation and are able to be formulated, or co-formulated with insulin (e.g., existing therapeutic insulin formulations), at neutral pH, the pharmacological formulations and mutant-hIAPP proteins of the present disclosure can be used in certain therapeutic applications.

As such, in another aspect of the present disclosure, the mutant-hIAPP polypeptide compositions disclosed herein are administered to a subject for the treatment of an abnormal condition for which the present mutant-hIAPP polypeptides can provide treatment, such as, for example, an amyloid-based disease, hyperglycemia and/or type-1 diabetes.

A "subject," used herein interchangeably with the term "patient," can be a human or any other mammal including, without limitation, a primate, rat, mouse, rabbit, pig, cow, sheep, goat, cat or dog. A "subject" as used herein, is any subject having a condition which, in the judgment of a practitioner (e.g., clinical or veterinarian), is indicative of a disease that can be treated by administration of a mutant-hIAPP polypeptide of the present disclosure. It is not necessary that the subject present any objectively or subjectively recognizable symptom of the disease to be "in need of treatment".

The term "therapy" used interchangeably herein with "treatment," refers to an attempt to prevent or ameliorate an abnormal condition, or the symptoms thereof, in a patient or a subject. It is not intended that "treating" a disease requires curing or eradicating it completely. It is only necessary that the treatment have a "therapeutic effect". Similarly, the progression of a disease is considered herein to be "reduced" or "inhibited" if, in the judgment of a practitioner, one or more of the characteristic indicia of progression of the disease are reduced or inhibited. The term "therapeutic effect" refers to the inhibition, activation or replacement of factors causing or contributing to an abnormal, pathological or pathogenic condition in a subject, such as, for example an amyloid-based disease. A therapeutic effect may or may not relieve all symptoms of the abnormal condition. A prophylactic or preventative effect delays the onset or reduces the severity of one or more of the symptoms or factors causing or contributing to the abnormal condition. In reference to the treatment of abnormal conditions, a "therapeutic effect" can refer, without limitation, to one or more of the following: (a) an increase or decrease in the proliferation, growth, and/or differentiation of cells or the products of cells (such as pancreatic β cells, or the hormones produced in pancreatic β cells) whether those products accumulate within the cells or are released therefrom, balancing blood glucose levels and gylcosylated hemoglobin levels; (b) enhancing or depressing the function of an affected cell or population of cells e.g., glycemic control, reducing amyloid deposits, which are formed in the islets of Langerhans of diabetic subjects are associated with reduced β-cell mass and are believed to contribute to type-2 diabetes.

An "abnormal condition" as used herein refers to a function in the cells or tissues of an organism that deviates from the normal function in that organism. An abnormal condition, by way of non-limiting examples, includes increased amyloid deposits in the islets of Langerhans of diabetic subjects, aberrant glycemic control, or dysregulation of hormones produced in pancreatic β cells. Abnormal cell products include metabolic products, hormones and other secreted products, cell signaling agents (whether intracellular or extracellular), elements of intracellular architecture including the cell membrane, "housekeeping" enzymes, and elements of the extracellular matrix. Abnormal cell survival conditions relate to, for example and without limitation, toxic agents of various types, both endogenous and exogenous, can induce cell death. In certain instances, the abnormal condition is type-1 diabetes or a disease characterized by the absence or abnormally reduced level of hIAPP even if that disease does not lead to amyloid formation.

The abnormal condition, such as a disease that can be prevented or treated with an identified agent and/or mutant-hIAPP polypeptide of the present disclosure by contacting such agent or mutant-hIAPP polypeptide to the cells or tissues of the subject.

In an exemplary embodiment of the present disclosure, an abnormal condition is an "amyloid based disease", which as used herein shall mean a pathological condition or disease characterized by the deposition of insoluble ordered protein deposits that are known as amyloid fibrils or amyloid plaques. Amyloid deposition or fibril formation is the pathological marker of many prevalent amyloid based diseases. In specific embodiments, amyloid-based diseases include, but are not limited to, amyloidoses (e.g., any disorder in which amyloid formation causes cell death, organ failure or disease). More particularly, the amyloidoses is type-2 diabetes, Alzheimer's Disease (AD), Parkinson's Disease (PD), dementia and cerebral amyloid angiopathy (CAA). In specific embodiments, amyloid-based diseases include, but are not limited to, amyloidoses (e.g., any disorder in which amyloid formation causes cell death, organ failure or disease). The presence of amyloid presents in a plethora of other amyloid based diseases, such as type-2 diabetes, Alzheimer's disease, bovine spongiform encephalopathy (BSE), Creutzfeldt-Jakob disease (CJD) and scrapie. Other examples of amyloid based diseases that can be treated using the present methods can be readily identified by those of ordinary skill in the art.

The term "aggregation," or "protein aggregates," used interchangeably herein, refers to a population of peptide molecules assembled into an insoluble deposit, which may have no discernible secondary structure, or may contain β-sheet structures, alpha-helices or other secondary structures. Secondary structure develops as the molecules orient themselves (evidently by intramolecular self-assembly) in strands lying side-by-side and attached by hydrogen bonds to form a so-called "β-sheet" that tends to grow along one axis into a "fibril." Fibrils are insoluble in aqueous solutions. That is, the monomers (and, perhaps, oligomers) that comprise them do not spontaneously return to their solvent as "solute" molecules. The fibrils tend to become entangled with one another to form "fibrillar tangles" and "dense core plaque," a late step in the process of fibrillization. Diffuse and dense core plaque, which may be referred to as "deposits" or "amyloid deposits," are insoluble. In certain circumstances, aggregation can occur without fibrillization of a peptide molecule and can lead to aggregates which contain other types of β-sheet structures, alpha-helical structure, or no discernable secondary structure (i.e., amorphous aggregates).

The intermolecular forces that hold fibrillizing peptides together in insoluble deposits or plaques are an aspect of "fibrillization" herein as are the intermolecular forces that urge dissolved monomers to aggregate. It will be understood that prevention of fibrillization need not be total to constitute "prevention" as used herein. The extent to which fibrillization has formed insoluble aggregates (or, interchangeably herein, "aggregations") may be evaluated by, for example, measuring in appropriately designed experiments the "thioflavin load" in the brain tissue of experimental animals or the amount of amyloid in the pancreas or other tissues. See Schmidt et al., *Am. J. Pathol*. (1995) 147 pp. 503-515 and Jurgens, C A et al., *Am. J. Pathol*. (2011) 178 pp 2632-2640.

Deficiencies in hIAPP also play an important role in non-amyloid based diseases such as type-1 diabetes and hyperglycemia. For example, in type-1 diabetes IAPP is not produced. Therefore, in one embodiment the present disclosure provides a method for the treatment of type-2 diabetes, hyperglycemia, or type-1 diabetes by administration of a pharmacological formulation including a mutant-hIAPP polypeptide.

In some embodiments, the mutant-hIAPP polypeptides administered to a subject include, but are not limited to, a mutant-hIAPP polypeptide that includes two of the following amino acid substitutions relative to the wild-type hIAPP amino acid sequence: N21K, N22K, N31K, N35K, N21R, N22R, N31R, N35R. In other embodiments, the mutant-hIAPP polypeptide includes two of the following amino acid substitutions relative to the wild-type hIAPP amino acid sequence: N21K, N22K, N31K, N35K, N21R, N22R, N31R, N35R, and a single Proline residue substitution at one of the following positions: 24, 25, 26, 28 or 29, such as those polypeptides set forth in SEQ ID NO: 11, SEQ ID NO: 17, SEQ ID NO: 12, SEQ ID NO: 18, SEQ ID NO: 15, SEQ ID NO: 19, SEQ ID NO: 13, SEQ ID NO: 20, SEQ ID NO: 14, SEQ ID NO: 21, SEQ ID NO: 16, and SEQ ID NO: 22. In other embodiments, the mutant-hIAPP polypeptide contains only the following amino acid substitutions relative to the wild-type hIAPP amino acid sequence: N21K, G24P, I26P, N35K as set forth in SEQ ID NO: 4 and SEQ ID NO: 8. In another specific embodiment, the mutant-hIAPP polypeptide contains only the following amino acid substitutions N22K, G24P, I26P, N31K as set forth in SEQ ID NOs: 6 and SEQ ID NO:10.

In one embodiment, the mutant polypeptide compositions are administered as part of a neutral pharmacological formulation, as described above. In specific embodiments, prior to administration the isolated mutant-hIAPP polypeptide of the present disclosure are formulated at a pH of from 6.8-7.4, 7.0-7.8, 7.4-7.8, and 7.0-7.4, inclusive. In certain specific embodiments, the mutant-hIAPP polypeptides of the present disclosure are formulated at a neutral pH of 7.2-7.4 or 7.4.

In some embodiments, the mutant-hIAPP polypeptide compositions of the present disclosure are co-formulated at neutral pH with at least one other therapeutic agent such as (e.g., insulin, Humalog®, Apidra®, NovoLog®, Humulin®, Novolin®, Novolin-N®, Levemir® or combinations thereof) and administered to a subject for the treatment of an amyloid-based disease. In certain embodiments, the mutant-hIAPP polypeptides of the instant disclosure are co-formulated at a neutral pH with a natural insulin or synthetic insulin and administered to a subject having an amyloid-based disease, such as type-2 diabetes or amyloidoses. In another embodiment, the mutant-hIAPP polypeptides of the instant disclosure are co-formulated at a neutral pH with an insulin and provided to a subject having type-1 diabetes or hyperglycemia.

The therapeutic methods of the present disclosure include administration by techniques known to exist in the art. Exemplary methods of administration include, but are not limited to oral, parenteral, dermal, injection, and aerosol applications. In some embodiments, the mutant polypeptide compositions or neutral formulations thereof are solutions that can be administered to a subject by injection. Injections, without limitation, may be made into the bloodstream, into cerebrospinal fluid, epidurally or subdurally, body cavities, and targeted disease sites (e.g., pancreas, intramuscular). In certain embodiments, the mutant polypeptide compositions or neutral formulations thereof are administered to a subject by intravenous injection, intraperitoneal injection, intramuscular injection, subcutaneous injection, or a combination thereof.

In certain embodiments, mutant-hIAPP polypeptide and/or agent(s) are administered to the subject such that the mutant-hIAPP polypeptide and/or agent(s) contact the cells or tissues of the subject. This may be accomplished, for example, by oral, parenteral, dermal, injection, and aerosol applications. Injections, without limitation, may be made into the bloodstream, into cerebrospinal fluid, epidurally or subdurally, body cavities, and targeted disease sites (e.g., pancreas). For example, various delivery systems are known and can be used to administer the mutant-hIAPP polypeptides of the present disclosure, formulations or co-formulations thereof, e.g., encapsulation in liposomes, microparticles, microcapsules, recombinant cells capable of expressing the compound, receptor-mediated endocytosis (see, e.g., Wu and Wu *J. Biol. Chem.* (1987) Vol. 262, pp. 4429-4432), and construction of a nucleic acid as part of a retroviral or other vector. Methods of introduction can be enteral or parenteral and include but are not limited to intradermal, intramuscular, intraperitoneal, intravenous, subcutaneous, intranasal, epidural, and oral routes. The agents and/or mutant-hIAPP polypeptides of the present disclosure may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the mutant-hIAPP polypeptides of the present disclosure or formulations thereof into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In another embodiment, the mutant-hIAPP polypeptides of the instant disclosure can be delivered in a vesicle, in particular a liposome (see Langer (1990) *Science* 249:1527-1533; Treat et al., *Liposomes in the Therapy of Infectious Disease and Cancer*, Lopez-Berestein and Fidler (eds.), Liss, N.Y., pp. 353-365 (1989); Lopez-Berestein, ibid., pp. 317-327; see, generally, ibid.)

In yet another embodiment, the mutant-hIAPP polypeptide of the present disclosure, formulations and co-formulations thereof can be delivered in a controlled release system. In one embodiment, a pump may be used (see Langer, supra; Sefton CRC Crit. Ref. Biomed. Eng. (1987) Vol. 14:201; Buchwald et al. *Surgery* (1980) Vol. 88:507; Saudek et al., *N. Engl. J. Med.* (1989) Vol. 321:574). In another embodiment, polymeric materials can be used (see Medical Applications of Controlled Release, Langer and Wise (eds), CRC Pres., Boca Raton, Fla. (1974); Controlled Drug Bioavailability, Drug Product Design and Performance, Smolen and Ball (eds.), Wiley, N.Y. (1984); Ranger and Peppas, J., 1983, *Macromol. Sci. Rev. Macromol. Chem.* Vol. 23:61; see, also, Levy et al. *Science* (1985) 228:190; During et al. *Ann. Neurol.* (1989) 25:351; Howard et al. *J. Neurosurg.* (1989) Vol. 71:105). In yet another embodiment, a controlled release system can be placed in proximity of the therapeutic target area, i.e., a target tissue, thus requiring only a fraction of the systemic dose (see, e.g., Goodson, in Medical Applications of Controlled Release, supra, (1984) Vol. 2, pp. 115-138). Other controlled release systems are discussed in the review by Langer, *Science* (1990) Vol. 249, pp. 1527-1533).

As such, in one embodiment, a subject having an amyloid-based disease is administered a therapeutically effective amount of an mutant-hIAPP polypeptide of the present disclosure, which reduces amyloid-based disease progression in the subject. In other embodiments of the present disclosure, a subject having type-1 diabetes or a disease characterized by the absence or abnormally reduced level of hIAPP is administered a therapeutically effective amount of an isolated mutant-hIAPP polypeptide of the present disclosure.

In certain instances, the mutant polypeptide compositions or neutral formulations thereof can be administered to a subject once a day, twice a day or more often. In some embodiments, the mutant polypeptide compositions or neutral formulations thereof are administered to a subject once a week, twice a week, three times a week, four times a week, 5 times a week, 6 times a week or more. In one embodiment, the mutant polypeptide compositions or neutral formulations thereof are administered to a subject by a pump, such as a portable infusion pump that can deliver a controlled or bolus amount of mutant polypeptide composition to a subject.

The dosage of a mutant-hIAPP polypeptide either alone or together with another therapeutic agent that is administered to a subject may vary depending on the reason for use, e.g., type of amyloid-based disease being treated or progression of the amyloid-based disease in a subject, hyperglycemia, type-1 diabetes, or obesity and the individual subject. For example, the dosage may be adjusted based on the subject's weight, the age and health of the subject, and tolerance for the mutant-hIAPP polypeptide and/or agent(s) being administered.

Certain, non-limiting examples of suitable dosage ranges for injection include, a dose of 0.06 mg/kg/day for an individual having a body weight of 40 kg or less, and such dose may increase or decrease by 0.02 mg/kg to a maximum daily dose of 0.13 mg/kg, a dose of 2.5 mg/day individual having a body weight greater than 40 kg, and such dose may increase or decrease by 1.25 mg to 2.5 mg/day to a maximum dose of 10 mg/day, for females having a body weight greater than 40 kg, a dose of 5 mg/day is appropriate, and such dose may increase or decrease by 1.25 mg to 2.5 mg/day to a maximum dose of 10 mg/day. In yet another example, the mutant-hIAPP polypeptide formulations of the present disclosure can be delivered to a subject in 30 mcg/mL, 60 mcg/mL, 90 mcg/mL or 120 mcg/mL doses.

In yet another embodiment, suitable dosage ranges for intranasal administration are generally about 0.01 pg/kg body weight to 1 mg/kg body weight. Effective doses may be extrapolated from dose-response curves derived from in vitro or animal model test systems.

Routine experimentation can determine the appropriate therapeutically effective amount to be administered to each subject. For example, a practitioner can monitor the mutant-hIAPP polypeptide and/or therapeutic agent(s) therapeutic effect on an abnormal condition e.g., disease progression and/or symptoms.

For example, after administration of the mutant-hIAPP polypeptide and/or agent(s), a practitioner can monitor one or more of the following physiological parameters associated with disease progression in the subject: (a) a change in the proliferation, growth, and/or differentiation of cells or the products of cells (such as pancreatic β cells, or the hormones produced in pancreatic β cells) whether those products accumulate within the cells or are released therefrom, blood glucose levels and gylcosylated hemoglobin levels; (b) altering the function of an affected cell or population of cells, e.g., glycemic control, reducing amyloid deposits, which are formed in the islets of Langerhans of diabetic subjects are associated with reduced β-cell mass and contribute to diabetes progression, and increase or decrease dosage of the hIAPP polypeptide and/or agent(s) to obtain the desired therapeutic effect.

The mutant-hIAPP polypeptide and/or agent(s) can be administered as needed, once or multiple times per day. The frequency of administration may vary from a single dose per day to multiple doses per day. In certain embodiments, the mutant-hIAPP polypeptide and/or agent(s) are added on an as needed basis such as, for example, when a subject with diabetes detects low blood glucose levels, or other symptoms present that would warrant administration of treatment.

EXAMPLES

Example 1

Materials and Methods

Peptide Synthesis. All peptides were synthesized on a 0.1 mmol scale using a CEM Liberty automated microwave peptide synthesizer. 9-fluornylmethoxycarbonyl (Fmoc) chemistry was utilized to create the mutant-hIAPP polypeptides of the present disclosure. The 5-(4'-fmoc-aminomethyl-3'5-dimethoxyphenol) valeric acid (PAL-PEG) resin was used to obtain an amidated C-terminus where applicable. For wild-type hIAPP (SEQ ID NO: 1), exemplary mutant-analog 1 (SEQ ID NO: 10), exemplary mutant-analog 2 (SEQ ID NO: 8), exemplary mutant analog 3 (SEQ ID NO: 7) and exemplary mutant analog 4 (SEQ ID NO: 22) Fmoc-protected pseudoproline (oxazolidine) dipeptide derivatives were incorporated to improve peptide yield as previously described in Abedini, A., and Raleigh, D. P. *Org. Lett*. (2005) Vol. 7, pp. 693-696, the entire contents of which are incorporated herein by reference. Standard Fmoc reaction cycles were used as previously described in Marek, P., et al. *Org. Lett*. (2010) Vol. 12, pp. 4848-4851, the entire contents of which are incorporated herein by reference. The first residue attached to the resin, all β-branched residues, all pseudoproline dipeptide derivatives were double-coupled. The peptides were cleaved from the resin through the use of standard trifluoroacetic acid (TFA) methods.

Oxidation and Purification of Peptides. Crude peptides collected after cleavage were dissolved into 20% (v/v) acetic acid and then freeze dried to increase solubility of the peptides. This step was repeated several times before oxidation and purification to improve the solubility of the peptides. The peptides were oxidized in 100% dimethyl sulfoxide at room temperature and then were purified via reverse-phase high-performance liquid chromatography (RP-HPLC) using a Vydac C18 preparative column. See, Abedini, A., et al. *Anal. Biochem*. (2006) Vol. 351, pp. 181-186.

A two buffer solution system was used. Buffer A was 100% $H_2O$ and 0.045% HCl and buffer B was 80% ACN (Acetonitrile), 20% $H_2O$ and 0.045% HCl. A gradient of 20% to 60% buffer B in 40 min was used. HCl was used as an ion pairing agent instead of TFA because TFA can influence amylin aggregation kinetics and can also affect amylin cell toxicity studies. The freeze dried peptides were dissolved in HFIP (1, 1, 1, 3, 3, 3-Hexafluoro-2-propanol) after the first purification to remove residual scavengers and re-purified with reversed-phase HPLC. The purity of the peptides was confirmed by reversed-phase HPLC using a C18 analytical column.

Sample Preparation. Each peptide was dissolved into 100% hexafluoroisoproponal (HFIP) to make a 0.5 mM stock solution. Stock solutions were filtered using 0.45 μM Acrodisc syringe filter with a GHP membrane and the required amount of peptide was lyophilized overnight to remove HFIP. Dry peptide was dissolved into the appropriate buffer for the fluorescence assays.

Fluorescence Assays. Thioflavin-T binding assays, conducted without HFIP or stirring at 25° C., were utilized to monitor amyloid formation kinetics. Fluorescence measurements were performed using a Spectramax Gemini EM plate reader. Corning 96-well non-binding surface black plates with lids were used and were sealed with polyethylene sealing tape. Samples were prepared by dissolving dry peptide into 10 mM PBS buffer (pH 7.4) and 32 μM thioflavin-T solution immediately before the measurement. Thioflavin-T fluorescence was measured with 450 nm excitation and emission at 485 nm was monitored. The final concentrations were 16 μM peptides.

Solubility Measurements. Dry peptides were dissolved into 10 mM PBS buffer at pH 7.4 at different initial concentrations, and were incubated for 7 days at 25° C. without stirring. Each sample was then centrifuged using a Beckman Coulter Microfuge 22R Centrifuge at 24° C. for 20 min. The relative centrifugal force used was $1.75 \times 10^4$ g. Solubility of each sample was approximated by measuring the absorbance of the corresponding supernatant at 280 nm measured using a Beckman Coulter DU 730 UV/Vis Spectrophotometer.

Transmission Electron Microscopy (TEM). TEM images were recorded using an FEI Bio TwinG$^2$ Transmission Electron Microscope at the central microscopy center at Stony Brook University. 15 μL aliquots of the samples used for fluorescence assays were removed at the end of each kinetic experiment, blotted on a carbon formvar-coated 300-mesh copper grid for 1 min and then negatively stained with saturated uranyl acetate for 1 min. Images were taken at a 68,000× magnification and 100 nm under focus.

Cell Culture and Transfection. Cos-7 cells were cultured and transfected for receptor activity assays as previously described in Bailey, R. J., and Hay, D. L. *Peptides* (2006) 27, pp. 1367-1375, the entire contents of which is incorporated herein by reference. Specifically, cells were cultured in Dulbucco's modified eagle medium (DMEM) with 8% heat-inactivated fetal bovine serum (FBS) and kept in a 37° C. humidified 95% air/5% $CO_2$ incubator. Cells were plated at a density of 18,000-20,000 cells/well (depending on cell passage) in 96-well culture plate and returned to the incubator for approximately 18-24 hours. Transient transfections were carried out using polyethyleneimine (PEI) as described previously and maintained at 37° C. in a humidified 95% air/5% $CO_2$ incubator for 36-48 hours. All DNA constructs used in this these were in pcDNA3.1 vectors.

cAMP Assay: Measurement of intracellular cAMP was achieved using a time-resolved fluorescent resonance energy transfer assay (LANCE cAMP assay, PerkinElmer), similar to the previously described Alphascreen assay as described in Gingell, J. J., et al. *Peptides* (2010) 31, pp. 1400-1404, with the following changes. Following stimulation with peptide agonist, cAMP assay media from the wells was thoroughly aspirated and 50 μl of ice-cold absolute ethanol added to each well. Plates were then placed in a −30° C. freezer for 10 minutes or overnight prior to assay, then removed and allowed to air dry in a fume hood for 1-2 hours. After ethanol evaporated from the plates, 50 μl of LANCE detection buffer (lysis buffer, 0.35% Triton X-100, 50 mM HEPES and 10 mM calcium chloride in dd$H_2O$, pH 7.4) was added per well and left on a plate shaker for 10-15 minutes at room temperature. Meanwhile, a cAMP standard curve was generated using LANCE detection buffer and a serially diluted cAMP standard (50 μM) ranging from 1 μM to 10 pM. The serially diluted cAMP standards (5 μl) and cell lysates (5 μl) were transferred into 384-well opti-plates and sealed with a Sealplate®-A-384-well microplate adhesive film and briefly centrifuged (10 seconds, 500 rpm, 23° C.). A 1:200 dilution of LANCE assay Alexa Fluor® 647 anti-cAMP antibody was prepared in detection buffer and 5 μl added to each well. Plates were sealed and briefly centrifuged again (10 seconds, 500 rpm, 23° C.) and left to incubate, sealed for 30 minutes at room temperature. During this incubation, detection mix was made up consisting of detection buffer, Europium-W8044 labelled streptavidin (1:4500) and biotin-cAMP (1:1500). After 30 minutes incubation, 10 μl of detection mix was added to each well, plates were centrifuged (30 seconds, 500 rpm, 23° C.), sealed and left to incubate for 1 hour at room temperature. Plates were read after an overnight incubation on an Envision plate reader. A standard curve was included in each experiment to ensure accurate quantification of cAMP.

Data Analysis for Receptor Assays: Data were derived from independent experiments for statistical analysis and all experiments were performed and replicated. Quantification of cAMP was obtained from a standard curve included in each experiment and plotted using the software GraphPad Prism 6.0 (GraphPad Software Inc, San Diego, Calif., USA) with a non-linear regression 3-parameter logistic equation with a Hill Slope of 1 to determine the $pEC_{50}$. The $pEC_{50}$ values from the fits were combined from different experimental days and statistically tested for difference from the WT peptide using the Student's t-test with statistical significance defined as * $p<0.05$,  $p<0.01$, * $p<0.001$. Due to variability in amount of cAMP produced between experimental days, data were normalized to the control peptide for each experiment to obtain $E_{max}$ values. For each analogue, data were normalized to the maximum ($E_{max}$) and minimum ($E_{min}$) responses of h-amylin. Normalized data for each experiment were combined and statistically tested for differences between analogs and the control h-amylin peptide by an unpaired Students t-test with statistical significance defined as * $p<0.05$,  $p<0.01$, * $p<0.001$.

Co-formulation with Insulin. Sufficient peptide, e.g., wild-type hIAPP, exemplary mutant-hIAPP polypeptides, and insulin were dissolved into 10 mM PBS buffer at pH 7.4 to give solutions with 500 μM per liter concentration of each peptide. The samples were incubated for 24 hours at 25° C. without stirring. Each sample was then centrifuged using a Beckman Coulter Microfuge 22R Centrifuge at 24° C. for 20 min. The relative centrifugal force used was $1.75 \times 10^4$ g. Aliquots were immediately frozen and lyophilized. Dry samples were redissolved in HPLC buffer (A:B, 4:1) and immediately injected for LC-UV-MS measurements. The HPLC buffers were (A) $H_2O$ (0.1% acetic acid and 0.02% TFA) and (B) $CH_3CN$ (0.1% acetic acid and 0.02% TFA). Solubility of each co-formulated sample was approximated by measuring the absorbance from liquid chromatogram trace at 215 nm at various time points (0 hours, and 24 hours post-formulation).

For experiments conducted to examine the solubility of mutant-hIAPP polypeptides with synthetic insulin peptide samples were dissolved in commercially available insulin, Novolin-N®. Sufficient peptide, e.g., wild-type hIAPP, exemplary mutant-hIAPP polypeptides, and pramlintide were dissolved into commercial human insulin formulation, Novolin-N® at pH 7 to provide solutions having a 600 μM concentration of each polypeptide tested. 100 μL each solution was obtained immediately following dissolution with Novolin-N® and was centrifuged using a Beckman Coulter Microfuge (22R Centrifuge) at 24° C. for 20 minutes. The relative centrifugal force used was $1.75 \times 104$ g. Aliquots of each sample were immediately frozen and lyophilized. The remaining portion of each sample was not centrifuged and were incubated at 25° C. without stirring. Samples were collected again following the same procedures after 1 day, 7 days and 30 days. Dry samples were redissolved in 4:1 HPLC buffer mix (4A:1B, below) and immediately injected for liquid chromatography-mass spectroscopy (LC-MS) measurements. The HPLC buffers were (A) H2O (0.1% acetic acid and 0.02% TFA) and (B) CH3CN (0.1% acetic acid and 0.02% TFA). Solubility of each co-formulated sample was determined by measuring the absorbance from the liquid chromatogram traces at 215±8 nm and at 277±8 nm at each time point tested. points (0 hours, 24 hours, 7 days and 30 days post-formulation).

Example 2

Mutant-hIAPP Polypeptides Do Not Form Amyloid

After creating the mutant-hIAPP polypeptides of the present disclosure, applicants tested the propensity of the different analogs to form amyloid at pH 7.4 using thioflavin-T fluorescence assays (FIGS. 2A-D) and TEM (FIGS. 3A-E). Thioflavin-T is a small dye that experiences an increase in quantum yield upon binding to amyloid fibrils, and has been shown to not perturb the kinetics of hIAPP formation. Amyloid formation follows a sigmoidal time course consisting of a lag phase in which few, if any, fibrils are formed, followed by a growth phase and a saturation phase in which amyloid fibrils are in equilibrium with soluble peptide. As seen in FIGS. 2A-D, amyloid formation by wild-type hIAPP reaches the saturation phase within 30 hours, while none of the 4 exemplary mutant-hIAPP analogs tested formed any amyloid during either 1 week or 6 week experiments, as indicated by flat fluorescence curves.

Mutant-hIAPP polypeptides of the present disclosure were further analyzed using TEM. TEM images of wild-type hIAPP showed typical amyloid fibril morphology after 1 week (FIG. 3A, left) and 6 week (FIG. 3A, right) time periods. In contrast, no amyloid fibrils were formed after a 1 week (FIGS. 3B-E, left) or 6 week (FIGS. 3B-E, right) culture with the any of the mutant-hIAPP analogs tested. Notably the 6 week TEM images (FIGS. 3A-E, right) show a precipitate from remnants of a metallic stain, which does not correspond to the formation of hIAPP aggregates. Hence, the TEM results are consistent with the thioflavin-T fluorescence experiments shown in FIGS. 2A-D.

Example 3

Mutant-hIAPP Polypeptides are Significantly More Soluble Than Wild-Type hIAPP at Neutral pH The solubility of exemplary mutant-hIAPP polypeptides of the present disclosure was analyzed and compared to that of the wild-type hIAPP protein and pramlintide at neutral pH. Each peptide tested was incubated in 10 mM PBS buffer at pH 7.4 for 7 days at three different concentrations (100 μM, 500 μM and 1 mM) and the solution was then centrifuged. The apparent solubility was represented by the absorbance of the supernatant of each sample measured at 280 nm. The extinction coefficients of all polypeptides are very similar at 280 nm since they all contain the same aromatic residues and each contains a disulfide bond. A sample of hIAPP at 1 mM was used as a control. A peptide which is soluble at 1 mM and above will show a linear dependence of absorbance on initial concentration. A peptide which is less soluble will deviate from linearity. The peptides were centrifuged after 7 days and their apparent solubility measured by measuring the absorbance at 280 nm of the supernatant of each solution. The apparent concentration refers to the concentration which would be obtained if all of the peptide dissolved. The absorbance of the supernatant is directly proportion to the amount of peptide in solution. Therefore, the higher the absorbance the more peptide remaining in solution. At all concentrations tested the mutant-hIAPP polypeptides exhibited a substantial increase in solubility over that of the wild-type hIAPP protein and a known hIAPP therapeutic peptide, pramlintide as shown by the absorbance in FIG. 4.

As shown in FIG. 6, the mutant-hIAPP polypeptides of the present disclosure can be co-formulated with natural insulin and remain in solution better than existing hIAPP based therapeutic peptides. The solubility of wild-type hIAPP (SEQ ID NO: 1) and an existing FDA approved hIAPP polypeptide (paramlintide; SEQ ID NO: 2) co-formulated with purified human insulin at neutral pH was compared to the solubility of exemplary mutant-hIAPP polypeptides co-formulated with insulin. The solubility of the peptides was measured by absorbance measurement at 277 nm using LC-MS. The exemplary mutant-hIAPP polypeptides tested (mutant analog 1, SEQ ID NO: 10; and mutant analog 2; SEQ ID NO: 16) exhibited a significantly higher absorbance when compared to both wild-type hIAPP and paramlintide when co-formulated at neutral pH. Taken together, the data shows that that the mutant-hIAPP polypeptides of the present disclosure are not only soluble when co-formulated with natural insulin at neutral pH, but are more soluble than wild-type hIAPP and other known therapeutic molecules when co-formulated with insulin at neutral pH.

Further, as shown in FIGS. 7A and 7B, when samples were co-formulated with commercially available synthetic insulin, Novolin-N® at a 1 to 1 ratio of of peptide to insulin reveal that each of the exemplary mutant-hIAPP polypeptides of the present disclosure remain soluble when formulated at a pH of 7 when mixed with synthetic insulin.

Taken together, these results clearly show that the exemplary mutant-hIAPP polypeptides of the present disclosure are significantly more soluble than wild-type hIAPP and pramlintide at neutral pH, whether or not they are co-formulated with an insulin.

Example 4

Mutant-hIAPP Polypeptides are Bioactive

In order to determine the therapeutic value of the mutant hIAPP polypeptides of the present disclosure, the bioactivity of exemplary mutant-hIAPP polypeptides was analyzed and compared to wild-type hIAPP bioactivity at human amylin receptors. Here, the biological activity of exemplary mutant-hIAPP polypeptides was measured by analyzing the production of cAMP at the $hCT_{(a)}$ and $hAMY_{1(a)}$ receptors in vitro according to the procedures previously described in Hay, D. L., et al. *Mol. Pharmacol.* (2005) 67, pp. 1655-1665 in order to determine amylin receptor activity. As shown in FIGS. 5A-D, stimulation of cAMP production occurred with both mutant-hIAPP analogs and wild-type hIAPP at both receptors. Notably, receptor response of cells expressing the mutant-hIAPP polypeptides of the present disclosure relative to wild-type hIAPP were similar for both amylin receptors analyzed.

Furthermore, the potency of the mutant-hIAPP polypeptides tested to act as agonists for the $hCT_{(a)}$ and $hAMY_{1(a)}$ receptors was compared to that of the wild-type hIAPP protein. As shown in Table I, the mutant-hIAPP polypeptides of the present disclosure modulate $hCT_{(a)}$ and $hAMY_{1(a)}$ receptors at levels similar to that of the wild-type hIAPP protein. In view of the foregoing, the mutant-hIAPP polypeptides of the present disclosure retain their biological activity in culture, and thus would make viable therapeutic agents.

TABLE 1

Receptor activity data shows that the mutant-hIAPP polypeptides of the present disclosure retain the ability to agonize the human calcitonin receptor and the human amylin receptor.

|  | Human calcitonin receptor binding data $pEC_{50}$ | Human Amylin$_{1(a)}$ receptor binding data $pEC_{50}$ |
|---|---|---|
| Wild-type hIAPP | 8.56 ± 0.21 | 9.86 ± 0.30 |
| SEQ ID NO: 7 | 8.62 ± 0.16 | 9.13 ± 0.18 |
| Wild-type hIAPP | 8.56 ± 0.21 | 9.86 ± 0.29 |
| SEQ ID NO: 8 | 7.97 ± 0.08 | 8.75 ± 0.25 |
| Wild-type hIAPP | 8.55 ± 0.18 | 9.47 ± 0.17 |
| SEQ ID NO: 10 | 8.30 ± 0.32 | 8.47 ± 0.20 |
| Wild-type hIAPP | 8.56 ± 0.21 | 9.86 ± 0.29 |
| SEQ ID NO: 22 | 8.55 ± 0.08 | 9.43 ± 0.33 |

Example 5

Mutant-hIAPP Polypeptides are Significantly More Soluble Than Wild-Type hIAPP When Co-Formulated With Insulin at Neutral pH The solubility of exemplary mutant-analog 1 and mutant-analog 2 polypeptides of the co-formulated with insulin was analyzed and compared to insulin co-formulated with wild-type hIAPP protein at neutral pH. Each peptide (wild-type and mutants) was incubated at a concentration of 500 µM per liter in 10 mM PBS buffer at pH 7.4 for 24 hours with an equal amount of insulin, and the solution was then centrifuged. The apparent solubility was represented by the absorbance of the supernatant of each sample measured at 215 nm. As shown in FIG. 6, all mutant-hIAPP polypeptides tested were significantly more soluble at neutral pH when co-formulated with insulin when compared to wild-type hIAPP/insulin co-formulations at all time points tested. Taken together, these results clearly show that the exemplary mutant-hIAPP polypeptides of the present disclosure can be co-formulated with insulin at neutral pH and maintain improved solubility over wild-type hIAPP.

What is claimed is:

1. An isolated mutant-human islet amyloid polypeptide hIAPP comprising an amino acid sequence that comprises at least two amino acid substitutions relative to the wild-type hIAPP polypeptide set forth in SEQ ID NO: 1 at positions 21, 22, 31 and 35, wherein said at least two amino acid substitutions comprise a substitution with lysine or arginine.

2. The isolated mutant-hIAPP of claim 1, wherein said mutant-hIAPP comprises an amino acid substitution at positions 21 and 35 relative to the wild-type hIAPP polypeptide set forth in SEQ ID NO: 1 as set forth in SEQ ID NOs: 3 or 7.

3. The isolated mutant-hIAPP of claim 1, wherein said mutant-hIAPP comprises an amino acid substitution at positions 22 and 31 relative to the wild-type hIAPP polypeptide set forth in SEQ ID NO: 1 as set forth in SEQ ID NOs: 5 or 9.

4. The isolated mutant-hIAPP of claim 1, wherein said mutant-hIAPP further comprises at least one proline substitution relative to the wild-type hIAPP polypeptide set forth in SEQ ID NO: 1 at positions 24, 26 or 28.

5. The isolated mutant-hIAPP of claim 4, wherein said mutant-hIAPP further comprises at least one proline substitution at position 24 or 26 relative to the wild-type hIAPP polypeptide set forth in SEQ ID NO: 1.

6. The isolated mutant-hIAPP of claim 4, comprising amino acid substitutions at positions 21 and 35 and a single proline substitution at position 24, 26 or 28 relative to the wild-type hIAPP polypeptide set forth in SEQ ID NO: 1.

7. The isolated mutant-hIAPP of claim 4, comprising amino acid substitutions at positions 22 and 31 and a single proline substitution at position 24, 26 or 28 relative to the wild-type hIAPP polypeptide set forth in SEQ II) NO: 1.

8. The isolated mutant-hIAPP of claim 4, wherein said mutant-hIAPP comprises an amino acid substitution at positions 22, 28 and 31 as set forth in SEQ. ID NOs: 16 or 22.

9. The isolated mutant-hIAPP of claim 4, wherein said mutant-hIAPP comprises an amino acid substitution at positions 21, 24, 26 and 35 as set forth in SEQ ID NOs: 4 or 8.

10. The isolated mutant-hIAPP of claim 4, wherein said mutant-hIAPP comprises an amino acid substitution at positions 22, 24, 26 and 31 as set forth in SEQ ID NOs: 6 or 10.

11. The isolated mutant-hIAPP of claim 1, wherein said isolated mutant-hIAPP is a synthetic peptide.

12. The isolated mutant-hIAPP of claim 1, wherein said isolated mutant-hIAPP is a recombinant peptide.

13. A pharmacological formulation comprising at least one of the isolated mutant-hIAPP of claim 1, wherein said pharmacological formulation has a neutral pH.

14. The pharmacological formulation of claim 13, wherein said neutral pH is between 7.0 and 7.8.

15. The pharmacological formulation of claim 13, wherein said neutral pH is 7.4.

16. The pharmacological formulation of claim 13, further comprising insulin.

17. The pharmacological formulation of claim 16, wherein said insulin is synthetic insulin.

18. A method for treating a subject comprising administering to the subject a therapeutically effective amount of an isolated mutant-hIAPP of claim 1, wherein said administration treats an abnormal condition in the subject, and wherein said abnormal condition is an amyloid based disease or type-1 diabetes.

19. The method of claim 18, further comprising administering to the subject a therapeutically effective amount of insulin, wherein said insulin and said isolated mutant-hIAPP is administered at neutral pH.

* * * * *